(12) United States Patent
Kato

(10) Patent No.: US 7,758,611 B2
(45) Date of Patent: Jul. 20, 2010

(54) DEVICE FOR TREATING A PATENT FORAMEN OVALE

(75) Inventor: Yukitoshi Kato, Kanagawa-ken (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1298 days.

(21) Appl. No.: 11/237,895

(22) Filed: Sep. 29, 2005

(65) Prior Publication Data

US 2006/0069408 A1    Mar. 30, 2006

(30) Foreign Application Priority Data

Sep. 29, 2004    (JP) .............................. 2004-285236

(51) Int. Cl.
*A61B 17/08* (2006.01)
(52) U.S. Cl. ........................ 606/213; 606/151; 606/215
(58) Field of Classification Search ................. 606/200, 606/213, 215, 151, 157
See application file for complete search history.

(56) References Cited

U.S. PATENT DOCUMENTS

| | | | |
|---|---|---|---|
| 5,662,681 A * | 9/1997 | Nash et al. ................... | 606/213 |
| 7,087,072 B2 * | 8/2006 | Marino et al. ................ | 606/213 |
| 7,288,105 B2 * | 10/2007 | Oman et al. ................ | 606/215 |
| 2003/0191495 A1 * | 10/2003 | Ryan et al. ................... | 606/213 |
| 2003/0225421 A1 | 12/2003 | Peavey et al. | |
| 2004/0143293 A1 * | 7/2004 | Marino et al. ................ | 606/213 |
| 2005/0273124 A1 * | 12/2005 | Chanduszko ................ | 606/159 |
| 2005/0277982 A1 * | 12/2005 | Marino et al. ................ | 606/213 |

FOREIGN PATENT DOCUMENTS

| | | |
|---|---|---|
| EP | 1 222 897 A2 | 7/2002 |
| WO | 02/098298 A1 | 12/2002 |

* cited by examiner

*Primary Examiner*—Darwin P Erezo
(74) *Attorney, Agent, or Firm*—Buchanan Ingersoll & Rooney PC

(57) ABSTRACT

A device for treating a patent foramen ovale has a first part having a predetermined length; a second part having a predetermined length; a third part having a predetermined length; and a pulling member which penetrates into the second part from a side face of a distal portion of the second part, crosses the second cylindrical part obliquely and extends from a side face of a proximal portion of the second part and penetrates into the third part from a side face of a distal portion of the third part, with one end of the pulling member held by a proximal portion of the first part. A part of a locking mechanism provided at other end of the pulling member and a part of the locking mechanism provided at the third part are locked to each other, when the pulling member is pulled to allow the first part and the second part proximate to each other and the second part and the third part to be proximate to each other.

10 Claims, 25 Drawing Sheets

DEVICE FOR TREATING A PATENT FORAMEN OVALE

BACKGROUND OF THE INVENTION

The present invention relates to a device and an apparatus for treating a patent foramen ovate by preventing an over-flap of the patent foramen ovate of a heart septum.

The foramen ovale is present in the interatrial septum. The foramen ovale works as a valve in a fetal heart Under normal conditions, the foramen ovale closes a few months after birth. The case in which the foramen ovate does not close after birth is called the patent foramen ovate. About 20% of adults have the patent foramen ovale. In a normal heart the internal pressure of the left atrium of heart is higher than that of the right atrium of heart, and the septum primum covers the foramen ovale as a valve. Therefore blood does not flow from the left atrium of heart to the right atrium of heart However, when the internal pressure of the right atrium of heart becomes higher than that of the left atrium of heart when a person becomes tense, the septum primum opens toward the left atrium of heart Thereby the blood flows from the right atrium of heart to the left atrium of heart When a thrombus is contained in venous blood flowing from the right atrium of heart to the left atrium of heart, the thrombus flows in the order of left atrium of heart→left ventricle→main artery→brain. Therefore the patent foramen ovale is said to be a cardiogenic factor of cerebral stroke and migraine.

The following treatments for the patent foramen ovate are performed: medicinal therapy (aspirin, warfarin), sealing surgery to be performed by using percutaneous catheter procedure, and open heart surgery to be performed by using extracorporeal circulation.

The medicinal therapy is the first-choice treatment for the patent foramen ovale. But it is difficult to control a dose and stop bleeding during administration. The percutaneous catheter procedure and the open heart surgery are invasive, but radical, thus giving no anxiety for a return. In the present stage, the open heart surgery is more reliable than the percutaneous catheter procedure in terms of the procedure of sealing the patent foramen ovale. But considering risks in performing the extracorporeal circulation and an invasion in incising skin, the percutaneous catheter procedure is more desirable than the open heart surgery if the percutaneous treatment provides an effect similar to that provided by the open heart surgery.

The device, for sealing the patent foramen ovale, which uses the percutaneous catheter procedure is retained at the portion of a congenital septal defect More specifically, to seal a hole in the septum, the procedure of retaining two disk-shaped films at the left atrium of heart and the right atrium of heart is adopted to sandwich the hole.

In the case of the cerebral stroke and the migraine, it is unnecessary to use the film to seal the septum primum which is usually sealed. In this case, it is possible to simplify the construction of the device. Retaining the device to cover the defect at the left atrium of heart and the right atrium of heart causes the thrombus to attach to the left atrium of heart and the like because the device has a large area. Thereby there is a possibility that the thrombus formed at the left atrium of heart causes a patient to have the cerebral stroke and that the device damages the thin septum primum. Thus there is a demand for development of a device of specific use.

To seal a hole of congenital diseases such as atrial septal defect (ASD), ventricular septal defect (VSD), and patent ductus arteriosus (PDA), the material for sealing septal defect is disclosed in EP1222897. The material for sealing septal defect is applicable to the patent foramen ovale. In using the material for sealing septal defect, the member is inserted into the hole by passing the member through the flap which is usually sealed. Thus there is a possibility that the frail septum primum is broken. Further because the member has a large area, there is a possibility that the thrombus attaches to the left atrium of heart or is discharged therein. Thus it is necessary to perform antiplatelet treatment to prevent the generation of the thrombus. As another problem of the method of using the material for sealing septal defect a large catheter is used because the disk-shaped material is accommodated in the catheter by folding it The device developed for carrying out this method is used specifically for a flap-shaped patent foramen ovale. Thus the risk of forming the thrombus is decreased by reducing the size of the member to be retained in a portion to be cured. When this method is used to perform antiplatelet treatment, effects such as reduction of a treatment period of time and a dose can be expected. Further it is possible to reduce the size of the catheter.

The clip-type device for sealing the patent foramen ovale for locking the flap is disclosed in U.S. patent Publication No. 2003/225421. In this device, the member shaped by using the material having a spring action is accommodated in the catheter by folding it. Folding the member to make the catheter small causes an excessive load to be applied to a bent portion. Thereby there is a possibility that the member loses the spring action and gives damage to the flap.

The device for sealing the patent foramen ovate is disclosed in WO2002/098298. The device nay also give damage to the flap.

It is an object of the present invention to provide an apparatus including a device, for treating a patent foramen ovate, which little damages a septum primum (flap) usually sealing the foramen ovale and little applies a load thereto, restrains the flap from opening toward the left atrium of heart, and is capable of preventing blood from flowing from the right atrium of heart to the left atrium of heart in spite of a patent foramen ovale.

SUMMARY OF THE INVENTION

The object described above is attained by the following a centrifugal fluid pump apparatus.

A device for treating a patent foramen ovale comprises a first part having a predetermined length, a second part having a predetermined length, a third part having a predetermined length, a pulling member penetrating into said second part from a side face of a distal portion of said second part, crossing said second cylindrical part obliquely and extends from a side face of a proximal portion of said second part, and penetrating or being penetrable into said third part from a side face of a distal portion of said third part, with one end of said pulling member held by said first part, and a pair of a locking mechanism provided at other end of said pulling member and said third part being locked to each other, when said pulling member is pulled to allow said first part and said second part to proximate to each other and said second part and said third part to be proximate to each other.

DETAILED DESCRIPTION OF THE PREFERRED EMBODIMENTS

The embodiments of a device of the present invention for treating a patent foramen ovale and an apparatus of the present invention for treating the patent foramen ovale will be described below with reference to drawings.

Figure 1:
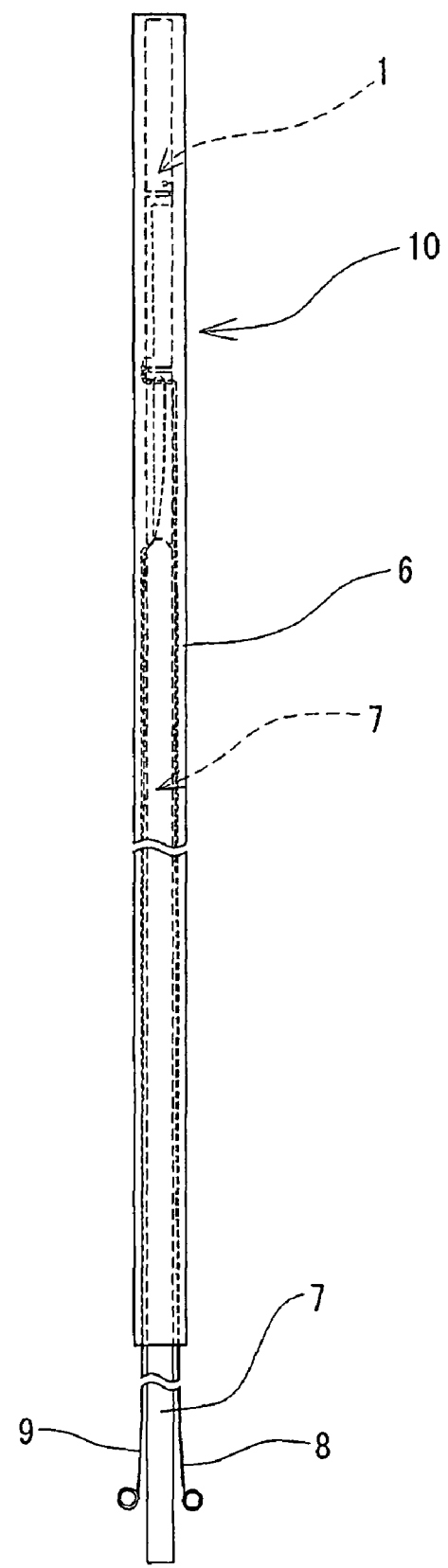
FIG. 1 is an outlook view of one embodiment of an apparatus, for treating a patent foramen ovale, including a device of the present invention for treating the patent foramen ovale.
Figure 2:
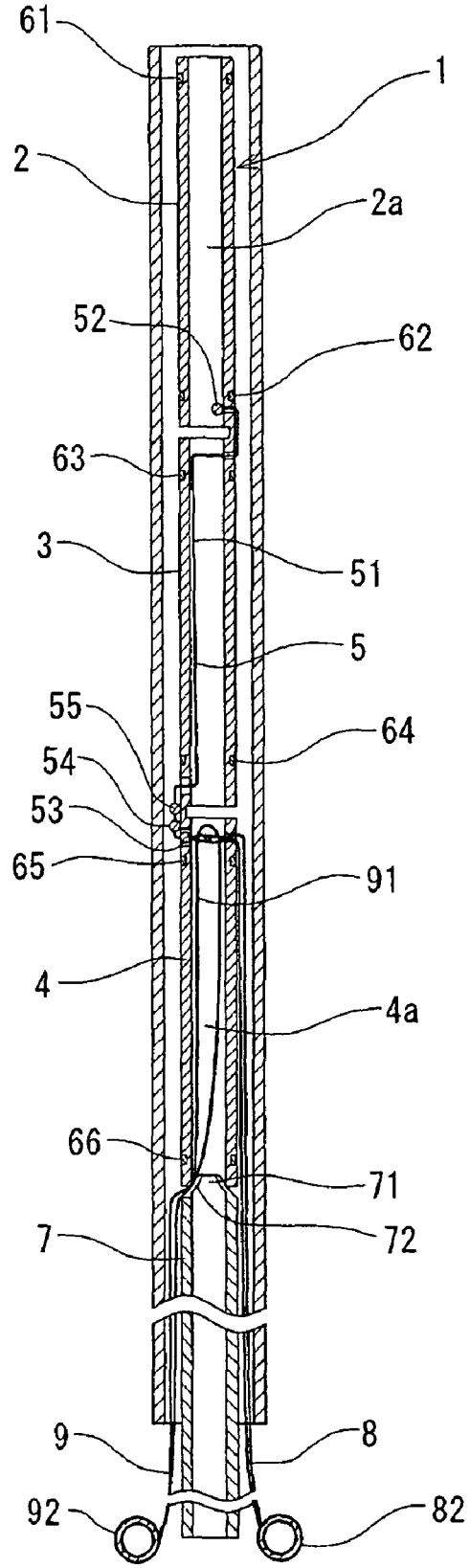
FIG. 2 is a partly omitted enlarged sectional view of the apparatus shown in FIG. 1.
Figure 3:
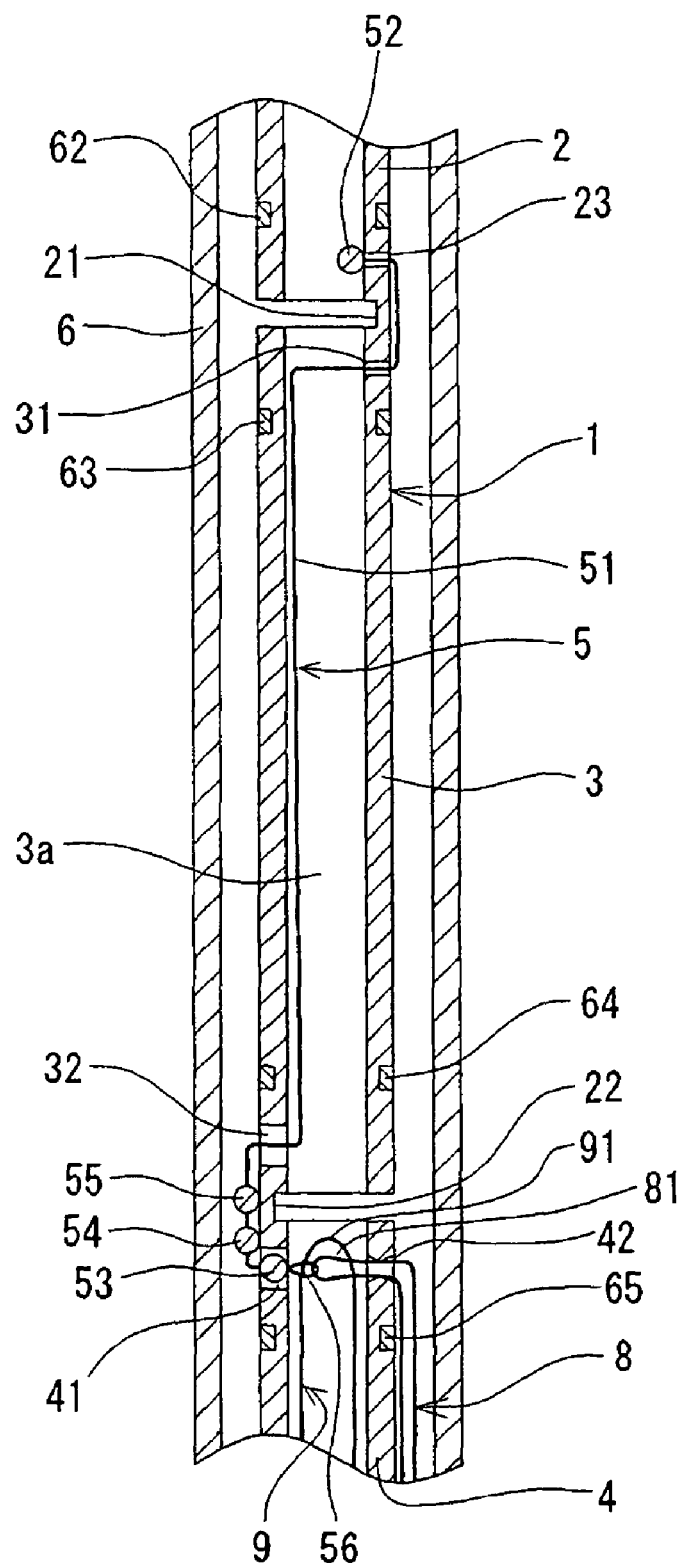
FIG. 3 is a partly enlarged sectional view of the apparatus shown in FIG. 1.

FIG. 1 is an outlook view of one embodiment of an apparatus, for treating a patent foramen ovale, including a device of the present invention for treating the patent foramen ovale. FIG. 2 is a partly omitted enlarged sectional view of the apparatus shown in FIG. 1. FIG. 3 is a partly enlarged sectional view of the apparatus shown in FIG. 1.

A device 1 for treating the patent foramen ovale (hereinafter often referred to as merely device 1) formed on a septum in an organism (in other words, a heart of human) has a first part 2 having a predetermined length; a second part 3 having a predetermined length; a third part 4 having a predetermined length; and a pulling member 5 which penetrates into the second part 3 from a side face of a distal portion of the second part 3, crosses the second cylindrical part 3 obliquely and extends from a side face of a proximal portion of the second part 3, and penetrates or is penetrable into the third part 4 from a side face of a distal portion of the third part 4, with one end of the pulling member 5 held by the first part 2. A part of a locking mechanism provided at other end of the pulling member 5 and a part of the locking mechanism provided at the third part 4 are locked to each other, when the pulling member 5 is pulled to allow the first part 2 and the second part 3 to be proximate to each other and the second part 3 and the third part 4 to be proximate to each other. In other words, the device 1 for treating the patent foramen ovale has a pair of the locking mechanism provided at other end of the pulling member 5 and the third part 4. The locking mechanism of the pulling member 5 and the locking mechanism of the third part 4 are locked to each other. Further in other words, the device 1 for treating the patent foramen ovale has a pair of the locking mechanism which comprises one of a part provided at the end of the pulling member 5 and the other of a part provided at the third part 4.

It is preferable that the first part is a first cylindrical or columnar part that the second part is a second cylindrical or columnar part, and that the third part is a third cylindrical or columnar part.

It is preferable that the device 1 has a first connection portion 21 bendably connecting a proximal end of the first part 2 and a distal end of the second part 3 to each other; and a second connection portion 22 bendably connecting a position, located at a proximal end of the second part 3, which confronts the first connection portion 21 obliquely and a distal end of the third part 4 to each other. It is preferable that with one end of the pulling member 5 held at a position of the first part 2 in the vicinity of the first connection portion 21, the pulling member 5 penetrates into the second part 3 from a position of the side face of the distal portion of the second part 3 in the vicinity of the first connection portion 21, extends from a position of the side face of the proximal portion of the second part 3 in the vicinity of the second connection portion 22, and penetrates into the third part 4 from a position of the side surface of the distal portion of the third part 4 in the vicinity of the second connection portion 22.

The apparatus 10 of the present invention has an outer tube 6, the device 1 accommodated inside a distal portion of the outer tube 6 with the device 1 kept almost straight an inner tube 7 for pressing the device 1 out of a distal end of the outer tube 6, and a pulling wire 8 for pulling the pulling member 5 separably from the pulling wire 8.

The apparatus 10 of the embodiment shown in FIGS. 1 through 3 will be described below.

The apparatus 10 of the embodiment has the outer tube 6, the device 1, the inner tube 7, and the pulling wire 8 for pulling the pulling member 5.

As shown in FIGS. 2 and 3, in the device 1 of this embodiment, the first part 2, the second part 3, and the third part 4 are constructed of a cylindrical part respectively and connected with each other. Therefore the device 1 of this embodiment has a first cylindrical part 2; a second cylindrical part 3; a third cylindrical part 4; a first connection portion 21 bendably connecting a proximal end of the first cylindrical part 2 and a distal end of the second cylindrical part 3 to each other; and a second connection portion 22 bendably connecting a position, located at a proximal end of the second cylindrical part 3, which confronts the first connection portion 21 obliquely and a distal end of the third cylindrical part 4 to each other. With one end of the pulling member 5 held at a position of the first cylindrical part 2 in the vicinity of the first connection portion 21, the pulling member 5 penetrates into the second cylindrical part 3 from a position of the side face of the distal portion of the second cylindrical part 3 in the vicinity of the first connection portion 21, extends from a position of the side face of the proximal portion of the second cylindrical part 3 in the vicinity of the second connection portion 22, and penetrates into the third cylindrical part 4 from a position of the side surface of the distal portion of the third cylindrical part 4 in the vicinity of the second connection portion 22. In other words, with one end of the pulling member 5 held at the proximal portion of the first cylindrical part 2, the pulling member 5 penetrates into the second cylindrical part 3 from the side face of the distal portion of the second cylindrical part 3, crosses the second cylindrical part 3 obliquely and extends from the side face of the proximal portion of the second cylindrical part 3, and penetrates into the third cylindrical part 4 from the side face of the distal portion of the third cylindrical part 4. A part of the locking mechanism provided at the other end of the pulling member 5 and a part of the locking mechanism provided at the third cylindrical part 4 are locked to each other, when the pulling member 5 is pulled to allow the first cylindrical part 2 and the second cylindrical part 3 to be proximate to each other and the second cylindrical part 3 and the third cylindrical part 4 to be proximate to each other.

More specifically, as shown in FIGS. 2 and 3, the first cylindrical part (first part) 2 has a side hole 23 disposed at its proximal portion. A slip-off prevention portion 52 provided at one end of the pulling member 5 is formed larger than the side hole 23. Thus when the pulling member 5 is pulled, the slip-off prevention portion 52 is held by an inner peripheral edge of the side hole 23. Regardless of whether the slip-off prevention portion 52 is provided at the one end of the pulling member 5, it may be fixed to the proximal portion of the first cylindrical part 2.

As shown in FIGS. 2 and 3, the second cylindrical part (second part) 3 has a side hole 31 provided at its distal portion and a side hole 32 provided at its proximal portion. The position of the side hole 32 and that of the side hole 31 are opposed to each other obliquely with respect to approximately the center of the second cylindrical part 3.

As shown in FIGS. 2 and 3, the third cylindrical part (third part) 4 has a side hole 41 formed at its distal portion and a locking side-hole 42 formed at a position opposed to the side hole 41.

The first cylindrical part 2, the second cylindrical part 3, and the third cylindrical part 4 have passageways 2a, 3a, and 4a respectively penetrating through the inside thereof These cylindrical parts 2, 3, and 4 may have any desired configurations. They may be circular, elliptic, square pillar-shaped, and the like. It is preferable that a guide wire can be inserted into the first cylindrical part 2, the second cylindrical part 3, and the third cylindrical part 4 when the pulling member 5 is present therein.

The outer diameter of each cylindrical part of the device 1 is favorably in the range from 0.1 mm to 5.0 mm and more favorably in the range from 1.0 mm to 3.0 mm. The inner diameter of each cylindrical part is favorably in the range from 0.02 mm to 4.9 mm and more favorably in the range from 0.4 mm to 2.8 mm. The length of each cylindrical part is favorably in the range from 5 mm to 50 mm and more favorably in the range from 7 mm to 35 mm.

As the material for forming each cylindrical part (first part, second part, and third part) of the device, in consideration of properties (flexibility, hardness, strength, sliding property, kink resistance, and stretching property) demanded therefor, it is preferable to selectively use polymers such as polyethylene, polypropylene, nylon, polyethylene terephthalate, fluorine-containing polymers (for example, PTFE, and ETFE); and thermoplastic elastomers. The thermoplastic elastomer includes synthetic resin of nylon family (for example, polyamide elastomer), urethane family (for example, polyurethane elastomer), polyester family (for example, polyethylene terephthalate elastomer), olefin family (for example, polyethylene elastomer, polypropylene elastomer); metals highly compatible with organisms such as titanium, titanium alloy, stainless steel, gold, and platinum.

It is preferable to treat the inner surface of each cylindrical part and particularly the inner surface of the second cylindrical part to enhance the sliding property of the pulling member. As such treatment, it is possible to adopt a method of applying or fixing the following hydrophilic polymers to the inner surface thereof: poly(2-hydroxyethyl methacrylate), polyhydroxyethyl acrylate, hydroxypropyl cellulose, methyl vinyl ether-maleic anhydride copolymer, polyethylene glycol, polyacryl amide, and polyvinyl pyrrolidone. To enhance the sliding property of the inner surface of the outer tube and/or the outer surface of the inner tube, these hydrophilic polymers may be applied or fixed thereto.

In the device 1 of this embodiment a part of the locking mechanism provided at the proximal portion of the pulling member 5 and a part of the locking mechanism provided at the third part 4 are locked to each other, when the pulling member 5 is pulled to allow the first part 2 and the second part 3 to be proximate to each other and the second part 3 and the third part 4 to be proximate to each other. More specifically, the locking mechanism is constructed of a to-be-locked anchoring portion of the pulling member 5 and the side hole 42 of the third cylindrical part 4 for locking the to-be-locked anchoring portion.

As shown in FIG. 3, the pulling member 5 has a linear portion 51; a holding portion 52 formed at the distal end of the linear portion 51 to hold the pulling member 5 at the first cylindrical part 2; and to-be-locked anchoring portions 53, 54, and 55 disposed at a proximal portion of the linear portion 51 along the linear portion 51. The linear portion 51 extends to the outside from the side hole 23 of the first cylindrical part 2, penetrates into the second cylindrical part 3 from the distal-side side hole 31 of the second cylindrical part 3, extends inside the second cylindrical part 3, and extends to the outside from the proximal-side side hole 32 of the second cylindrical part 3. The to-be-locked anchoring portions 53, 54, and 55 provided at the proximal portion of the pulling member 5 are disposed outside the third cylindrical part 4 or a part thereof penetrates into the third cylindrical part 4 from the distal-side side hole 41 of the third cylindrical part 4. As shown in FIG. 3, the proximal end of the pulling member 5 may penetrate into the third cylindrical part 4 from the distal-side side hole 41 of the third cylindrical part 4 or may be disposed on the outer surface of the third cylindrical part 4.

As the material for forming the linear portion of the pulling member and the to-be-locked anchoring portion thereof, it is possible to use metals such as stainless steel, Ni—Ti alloy, Cu—Zn alloy, Ni—Al alloy, tungsten, tungsten alloy, titanium, titanium alloy, cobalt alloy, tantalum; comparatively rigid polymeric materials such as polyamide, polyimide, ultra-high-molecular-weight polyethylene, polypropylene, fluororesin; and a combination of these materials. As the linear portion 51, a wire or a plurality of twisted wires can be preferably used. Although not specifically limited, the diameter of the linear portion is favorably in the range from 0.01 mm to 1.3 mm and more favorably in the range from 0.1 mm to 0.3 mm.

In this embodiment, the locking mechanism of the embodiment is composed of a plurality of the to-be-locked anchoring portions 53, 54, and 55 provided at the other end portion (proximal portion) of the pulling member 5 and the locking side-hole 42 provided at the third cylindrical part 4. The locking side-hole 42 has a small portion permitting a forced passage of the anchoring portion and locking the anchoring portion thereto after the anchoring portion passes therethrough More specifically, the locking side-hole 42 has a small diameter portion whose inner diameter is smaller than the outer diameter of the anchoring portion. The inner diameter of the locking side-hole 42 is smallest at its central portion to form the small-diameter portion. The inner diameter of both sides inward and outward from the small-diameter portion becomes gradually larger. Thereby the locking side-hole 42 facilitates the forced passage of the anchoring portion therethrough and holds the anchoring portion securely. Although it is preferable that the small diameter portion has the above-described construction, the small-diameter portion may be composed of an annular rib or ribs annularly dotted. The small-diameter portion may be disposed on the inner side of the locking side-hole 42 or on the outer side thereof.

In this embodiment the to-be-locked anchoring portions 53, 54, and 55 are provided at the proximal portion of the linear portion 51 of the pulling member 5 along the linear portion 51. The to-be-locked anchoring portions 53, 54, and 55 can be locked to the locking side-hole 42. Thereby by locking the to-be-locked anchoring portion 54 to the locking side-hole 42, it is possible to shorten the distance between the first cylindrical part 2 and the second cylindrical part 3 and the distance between the second cylindrical part 3 and third cylindrical part 4, compared with the case where the to-be-locked anchoring portion 53 is locked to the locking side-hole 42. Similarly by locking the to-be-locked anchoring portion 55 to the locking side-hole 42, it is possible to shorten the distance between the first cylindrical part 2 and the second cylindrical part 3 and the distance between the second cylindrical part 3 and third cylindrical part 4 to a higher extent, compared with the case where the to-be-locked anchoring portion 54 is locked to the locking side-hole 42. Therefore the device of this embodiment allows adjustment of the distance between the first cylindrical part 2 and the second cylindrical part 3 and the distance between the second cylindrical part 3 and third cylindrical part 4 by selectively locking the to-be-locked anchoring portion to the locking side-hole in dependence on the thickness of the flap of the septum primum or the configuration of the foramen ovale.

As shown in FIGS. 1, 2, and 3, the outer tube 6 is tubular. The outer tube 6 is open at its distal and proximal ends. The opening formed at the distal end of the outer tube 6 functions as a release opening when the device 1 is retained in a foramen ovale. The distal portion of the outer tube 6 serves as an accommodation portion for accommodating the device 1 therein when the device is straight.

The outer diameter of the outer tube 6 is favorably in the range from 0.3 mm to 7.0 mm and more favorably in the range from 1.2 mm to 5.0 mm. The inner diameter of the outer tube 6 is favorably in the range from 0.2 mm to 6.5 mm. The length of the outer tube 6 is favorably in the range from 300 mm to 2000 mm and more favorably in the range from 700 mm to 1500 mm.

As shown in FIGS. 1 through 3, the inner tube 7 is tubular. The inner tube 7 is open at its distal and proximal ends. The guide wire can be inserted through the inner tube 7. The inner tube 7 is accommodated in the outer tube 6. The distal portion 71 of the inner tube 7 is capable of contacting the proximal portion of the device 1. Thus the inner tube 7 is capable of pressing the device 1 from the distal end of the outer tube 6. As shown in FIG. 2, in the apparatus 10 of this embodiment, the diameter of the distal portion 71 of the inner tube 7 becomes gradually smaller toward its distal end to allow the distal portion 71 of the inner tube 7 to penetrate into the proximal portion of the device 1. Provided at the distal portion 71 of the inner tube 7 is a slit 72 into which an unlocking wire is inserted. The unlocking wire constructs an unlocking mechanism for releasing locking performed by the locking mechanism (described later) of the device 1.

The outer diameter of the inner tube 7 is favorably in the range from 0.1 mm to 5.0 mm and more favorably in the range from 1.0 mm to 3.0 mm. The inner diameter of the inner tube 7 is favorably in the range from 0.05 mm to 4.8 mm. The length of the inner tube 7 is favorably in the range from 300 mm to 2000 mm and more favorably in the range from 700 mm to 1500 mm.

As the material for forming the outer tube 6 and the inner tube 7, in consideration of properties (flexibility, hardness, strength, sliding property, kink resistance, and stretching property) demanded for them, it is preferable to selectively use polymers such as polyethylene, polypropylene, nylon, polyethylene terephthalate, fluorine-containing polymers (for example, PTFE, and ETFE); and thermoplastic elastomers. The thermoplastic elastomer includes synthetic resin of nylon family (for example, polyamide elastomer), urethane family (for example, polyurethane elastomer), polyester family (for example, polyethylene terephthalate elastomer), olefin family (for example, polyethylene elastomer, polypropylene elastomer).

It is preferable to treat the outer surface of the outer tube 6 to enhance the sliding property thereof. As such treatment it is possible to adopt a method of applying or fixing the following hydrophilic polymers to the inner surface thereof: poly(2-hydroxyethyl methacrylate), polyhydroxyethy acrylate, hydroxypropyl cellulose, methyl vinyl ether-maleic anhydride copolymer, polyethylene glycol, polyacryl amide, and polyvinyl pyrrolidone. To enhance the sliding property of the inner surface of the outer tube and/or the outer surface of the inner tube, these hydrophilic polymers may be applied or fixed thereto.

The apparatus 10 has a pulling wire 8 for pulling the pulling member. The pulling wire 8 extends from the proximal side of the apparatus 10 between the inner tube 7 and the outer tube 6. The distal portion of the pulling wire 8 penetrates into the third cylindrical part 4 from the locking side-hole 42 of the third cylindrical part 4. The proximal portion of the pulling wire 8 extends to the outside from the proximal end of the outer tube 6. The pulling wire 8 is separable from the pulling member. As shown in FIG. 3, the pulling member 5 of the device 1 has an annular portion 56 at its proximal end. The pulling wire 8 is folded back after it penetrates through the annular portion 56. That is, a looped portion 81 of the pulling wire 8 is in penetration through the annular portion 56. By pulling the pulling wire 8 (exactly, two wires), the pulling member 5 is pulled to the proximal side of the apparatus 10.

An operation portion 82 is mounted at the proximal end (proximal end of two wires) of the pulling wire 8. The pulling wire 8 is made of a material which can be cut Alternatively the operation portion 82 can be removed from the pulling wire 8. Therefore by cutting the pulling wire 8 or removing the operation portion 82 from the pulling wire 8, the end of the pulling wire 8 is formed or exposed. By pulling the pulling wire 8, the pulling wire 8 can be separated from the pulling member 5. Instead of the annular portion 56, the pulling member 5 may have a hole through which the pulling wire 8 can be inserted.

The apparatus 10 has the unlocking mechanism for releasing locking performed by the locking mechanism of the device 1. The unlocking mechanism of the apparatus 10 is composed of the unlocking wire 9, having a loop 91, which is disposed in the apparatus 10. The pulling member 5 of the device 1 or the pulling wire 8 thereof is in penetration through the loop 91 of the unlocking wire 9. Thus by pulling the unlocking wire 9 toward the proximal side of the device 1, with the anchoring portion 53 being locked to the locking side-hole 42, the anchoring portion 53 is forcibly passed through the locking side-hole 42 and is returned to the inside of the third cylindrical part 4. Thereby the anchoring portion 53 and the locking side-hole 42 are unlocked from each other. An operation portion 92 is mounted at the proximal end (proximal end of two wires) of the unlocking wire 9. The unlocking wire 9 is made of a material which can be cut Alternatively the operation portion 92 can be removed from the unlocking wire 9. Therefore by cutting the unlocking wire 9 or removing the operation portion 92 from the unlocking wire 9, the end of the unlocking wire 9 is formed or exposed. By pulling the unlocking wire 9, the unlocking wire 9 can be separated from the pulling member or the pulling wire.

As the pulling wire and the unlocking wire, a wire or a plurality of twisted wires can be preferably used. Although not specifically limited, the diameter of the pulling wire and the unlocking wire is favorably in the range from 0.1 mm to 1.3 mm and more favorably in the range from 0.1 mm to 0.3 mm. As the material for forming the pulling wire and the unlocking wire, it is possible to use metals such as stainless steel, Ni—Ti alloy, Cu—Zn alloy, Ni—Al alloy, tungsten, tungsten alloy, titanium, titanium alloy, cobalt alloy, tantalum; comparatively rigid polymeric materials such as polyamide, polyimide, ultra-high-molecular-weight polyethylene, polypropylene, fluororesin; and a combination of these materials.

As shown in FIGS. 2, 3, 16, and 17, a contrast portion 61 is formed at the distal portion of the first cylindrical part 2. A contrast portion 62 is formed at the proximal portion of the first cylindrical part 2. A contrast portion 63 is formed at the distal portion of the second cylindrical part 3. A contrast portion 64 is formed at the proximal portion of the second cylindrical part 3. It is preferable to provide both the contrast portions 62 and 63, but the formation of one of the contrast portion 62 and the contrast portion 63 may be omitted. A contrast portion 65 is formed at the distal portion of the third cylindrical part 4. A contrast portion 66 is formed at the proximal portion of the third cylindrical part 4. It is preferable to provide both the contrast portions 64 and 65, but the formation of one of the contrast portion 64 and the contrast portion 65 may be omitted. In the examples shown in FIGS. 2, 3, 16, and 17, the contrast portions are formed at positions a little inward from the distal or proximal ends of the cylindrical parts, but may be formed at the distal or proximal ends of the cylindrical parts.

The positions of these contrast portions can be checked by X-ray contrast and ultrasonic wave contrast. It is preferable to compose the contrast portion of a ring-shaped wire or a coiled linear wire. As the material of the contrast portion, gold, platinum, tungsten, and alloys of these metals, a silver-palladium alloy can be preferably used. The contrast portion may be made of the same material as that used for the cylindrical members or a combination of a contrast substance and a material compatible therewith. As the contrast substance, it is possible to use X-ray unpermeable materials such as barium sulfate, bismuth oxide, and tungsten. A contrast portion (not shown) may be formed at the distal portion of the outer tube 6. It is possible to form the contrast portion at the distal portion of the outer tube 6 by a method similar to the method of forming the above-described contrast portions.

Figure 4:
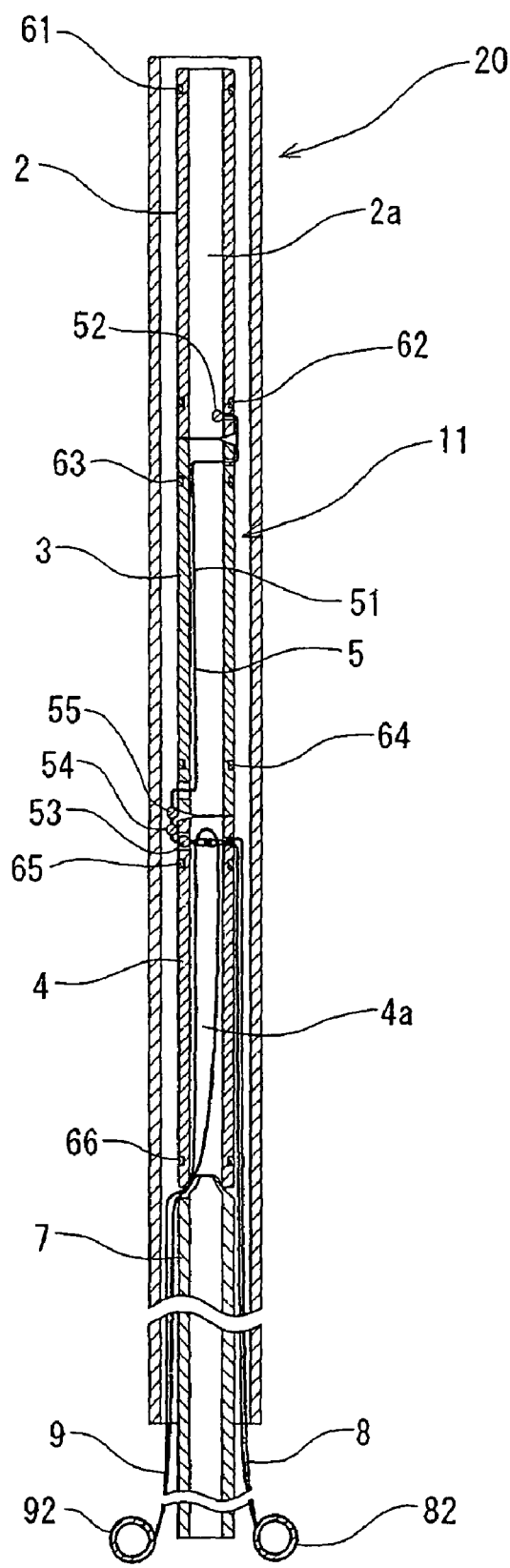
FIG. 4 is a partly omitted enlarged sectional view of another embodiment of an apparatus, for treating the patent foramen ovale, including a device of the present invention for treating the patent foramen ovale.

An embodiment of an apparatus 20 for treating the patent foramen ovale having a device for treating the patent foramen ovale shown in FIG. 4 is described below.

Figure 5:
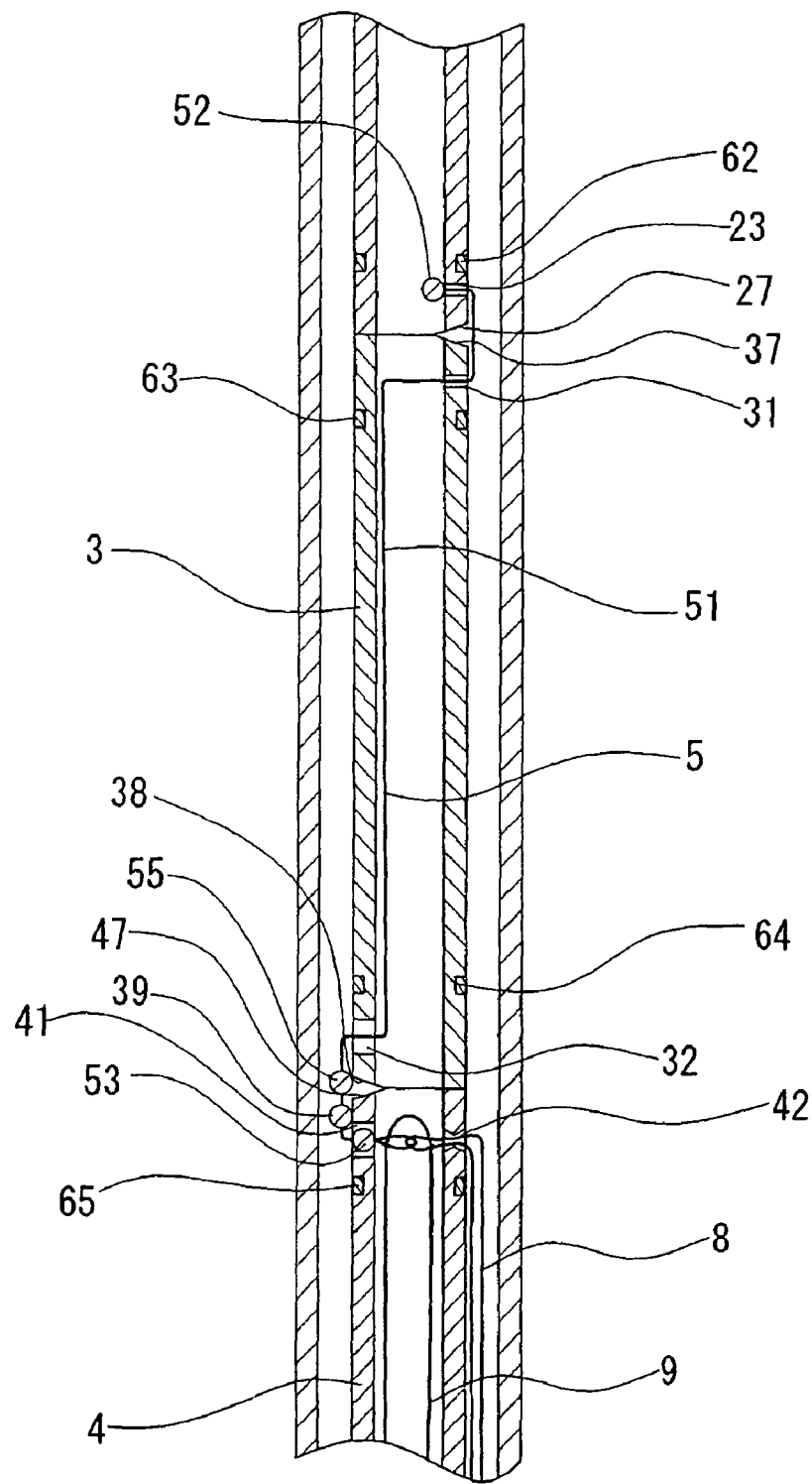
FIG. 5 is a partly enlarged sectional view of the apparatus shown in FIG. 4.

FIG. 4 is a partly omitted enlarged sectional view of another embodiment of an apparatus, for treating the patent foramen ovale, including a device of the present invention for treating the patent foramen ovale. FIG. 5 is a partly enlarged sectional view of the apparatus shown in FIG. 4.

In the above-described device 1, the first part (first cylindrical part) 2 and the second part (second cylindrical part) 3 are connected to each other with the first connection portion, and the second part (second cylindrical part) 3 and the third part (third cylindrical part) 4 are connected to each other with the second connection portion. The apparatus 20 is different from the above-described apparatus 10 in that in a device 11 of this embodiment, the first part (first cylindrical part) 2, the second part (second cylindrical part) 3, and the third part (third cylindrical part) 4 are not connected to one another. In other words, the first part (first cylindrical part) 2, the second part (second cylindrical part) 3, and the third part (third cylindrical part) 4 are separately provided. The other constructions of the device 11 are similar to those of the device 1 of the above-described embodiment. Thus the same parts of this embodiment as those of the above-described embodiment are denoted by the same reference numerals as those of the above-described embodiment, and the above-described descriptions are referred to. In the device 11 of this embodiment, the first cylindrical part 2 has an inclined face 27 formed on a bottom surface of the proximal end thereof in the vicinity of the proximal-side side hole 23. The second cylindrical part 3 has an inclined face 37 formed on an upper surface of the distal end thereof in the vicinity of the distal-side side hole 31 and an inclined face 38 formed on a bottom surface of the proximal end thereof in the vicinity of the proximal-side side hole 32. The third cylindrical part 4 has an inclined face 47 formed on an upper surface of the distal end thereof in the vicinity of the distal-side side hole 41. The first cylindrical part 2 and the second cylindrical part 3 are so disposed that the inclined face 27 of the first cylindrical part 2 and the inclined face 37 of the second cylindrical part 3 confront each other. The second cylindrical part 3 and the third cylindrical part 4 are so disposed that the inclined face 38 of the second cylindrical part 3 and the inclined face 47 of the third cylindrical part 4 confront each other. Therefore when the pulling member 5 is pulled, each cylindrical member can be inclined easily.

Figure 6:
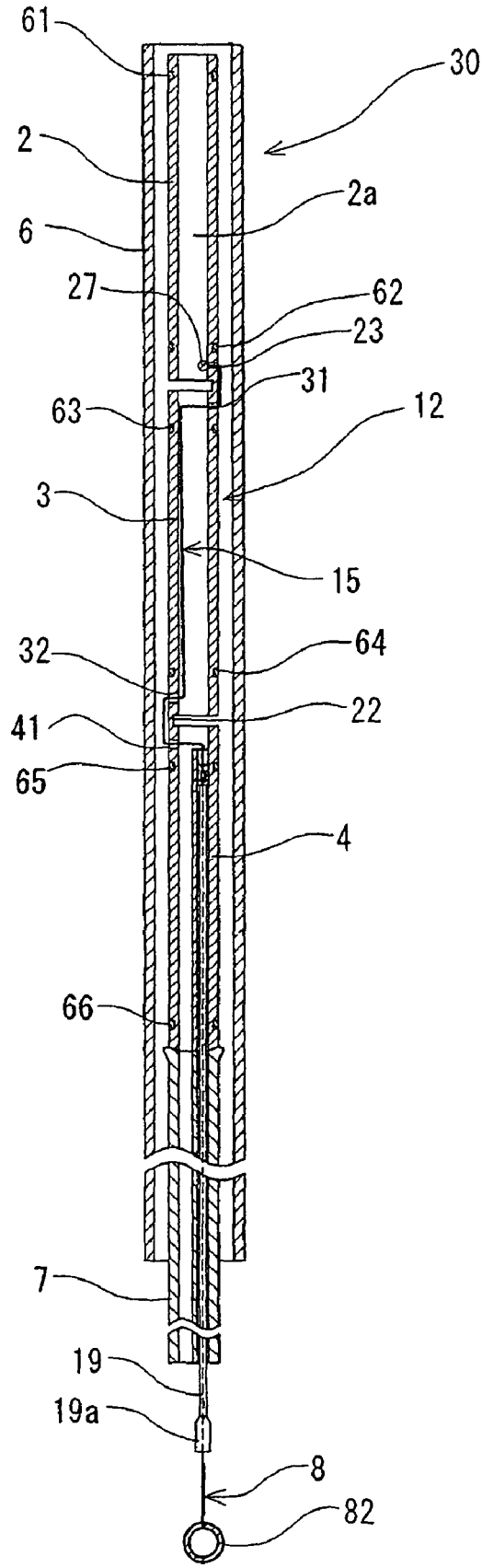
FIG. 6 is a partly omitted enlarged sectional view of another embodiment of an apparatus, for treating the patent foramen ovale, including a device of the present invention for treating the patent foramen ovale.

An embodiment of an apparatus 30 for treating the patent foramen ovale having a device for treating the patent foramen ovale shown in FIG. 6 is described below.

Figure 7:
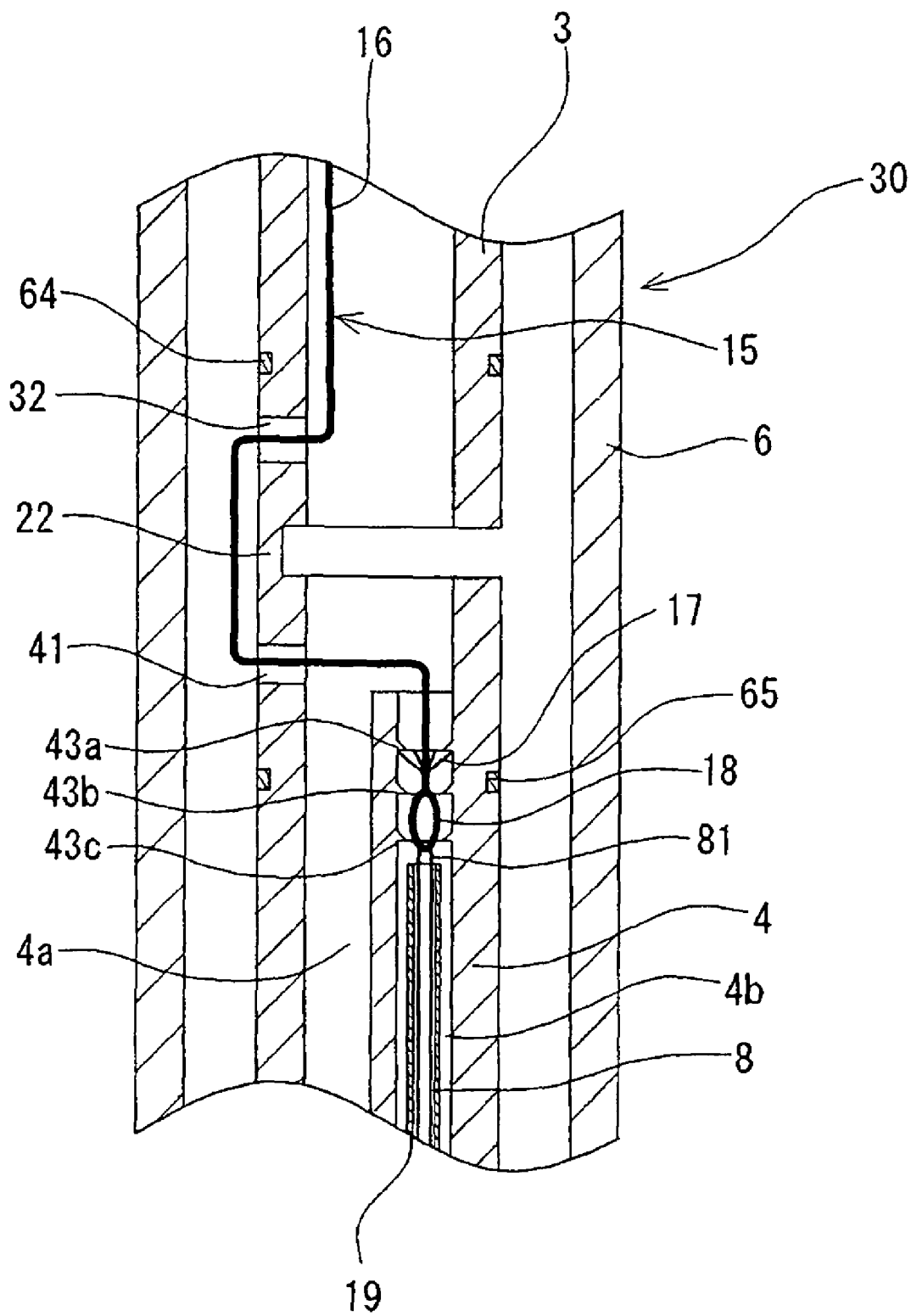
FIG. 7 is a partly enlarged sectional view of the apparatus shown in FIG. 6.

FIG. 6 is a partly omitted enlarged sectional view of another embodiment of an apparatus, for treating the patent foramen ovale, including a device of the present invention for treating the patent foramen ovale. FIG. 7 is a partly enlarged sectional view of the apparatus shown in FIG. 6.

A device 12 of the apparatus 30 is different from the device 1 of the apparatus 10 in the inner configuration of the third cylindrical part 4, the locking mechanism for locking a pulling member 15 including the form of an anchoring portion 17 to a locking portion of the third cylindrical part 4, and the unlocking function. The other constructions of the device 12 are similar to those of the device 1 of the above-described embodiment Thus the same parts of this embodiment as those of the above-described embodiment are denoted by the same reference numerals as those of the above-described embodiment and the above-described descriptions are referred to.

The locking mechanism of the device 30 of this embodiment is constructed of an anchor 17 of a pulling member 15 and a locking portion 43 provided on a side face of a second passageway 4b of the third cylindrical part 4.

As shown in FIGS. 6 and 7, in the device 12 of the apparatus 30, the third cylindrical part 4 has two lumens extending in parallel with each other. As described above, a first passageway 4a serves as a guide wire insertion passageway. Inside the distal portion of the second passageway 4b, the second passageway 4b has a locking portion 43 to which the anchoring portion 17 of the pulling member 15 is locked. In this embodiment, locking portions 43a, 43b, and 43c are formed at certain intervals along the axial direction of the second passageway 4b. The locking portions 43a, 43b, and 43c are constructed of an annular rib respectively. Each of the locking portions 43a, 43b, and 43c has an annular inclined face for guiding the anchoring portion 17 whose inner diameter becomes gradually shorter from its distal side to its proximal side; and an annular face disposed at the rear end of the annular inclined face and being orthogonal to the second passageway 4b. The annular face and the anchoring portion 17 are locked to each other.

As in the case of the above-described embodiment, the pulling member 15 has a holding portion formed at the distal end thereof to hold the pulling member 15 at the first cylindrical part 2. As shown in FIGS. 6 and 7, the pulling member 15 extends to the outside from the distal-side side hole 23 of the first cylindrical part 2, penetrates into the second cylindrical part 3 from the distal-side side hole 31 of the second cylindrical part 3, extends inside the second cylindrical part 3, extends to the outside from the proximal-side side hole 32 of the second cylindrical part 3, penetrates into the third cylindrical part 4 from the distal-side side hole 41 of the third cylindrical part 4. The proximal portion of the pulling member 15 is disposed inside the second passageway 4b. The proximal portion of the pulling member 15 may not penetrate into the third cylindrical part 4 but may be disposed on the outer surface of the third cylindrical part 4. The anchoring portion 17 of this embodiment has a construction similar to that of an umbrella rib. More specifically, the proximal end of the anchoring portion 17 is fixed to the pulling member, and the distal end thereof is formed as a free end. That is, the anchoring portion 17 is constructed of a plurality of rod-shaped members that can be folded back toward its distal side. The rod-shaped members extend radially and obliquely from a given position of the pulling member 15 toward the distal end thereof. Therefore by folding the anchoring portion 17 toward the distal side thereof, it is capable of passing through the locking portions 43a, 43b, and 43c. After passing through the locking portions 43a, 43b or 43c, the anchoring portion 17 opens (in other words, returns to the open configuration), and the distal end thereof is locked to the annular face of the locking portion. An annular portion 18 is provided at the proximal portion of the pulling member 15. Instead of providing the pulling member 15 with the annular portion 56, the pulling member 15 may be so constructed that the anchoring portion 17 thereof has a hole into which the pulling wire 8 can be inserted or the anchoring portion 17 is pulled by the pulling wire 8. The locking portion 43 may be constructed of an annular groove instead of the annular rib.

Similarly to the above-described apparatus 10, the apparatus 30 of this embodiment has a pulling wire 8 for pulling the pulling member. In correspondence with the inner construction of the third cylindrical part 4, the inner tube 7 has two lumens extending therein in parallel. A guide wire is inserted through a first lumen corresponding to the first passageway 4a of the third cylindrical part 4. An unlocking wire 19 and the pulling wire 8 are inserted through a second lumen corresponding to the second passageway 4b of the third cylindrical part 4. The pulling wire 8 extends inside the second lumen of the inner tube 7 and penetrates into the third cylindrical part 4 from the distal end of the second passageway 4b of the third cylindrical part 4. The proximal portion of the pulling wire 8 extends to the outside from the proximal end of the inner tube 7. The pulling wire 8 is separable from the pulling member 15. As shown in FIG. 6, the pulling member 15 of the device 12 has the annular portion 18 at its proximal end. The pulling wire 8 is folded back after it penetrates through the annular portion 18. That is, the looped portion 81 of the pulling wire 8 is in penetration through the annular portion 18. By pulling the pulling wire 8 (exactly, two wires), the pulling member 15 is pulled to the proximal side of the apparatus 30. An operation portion 82 is mounted at the proximal end (proximal end of two wires) of the pulling wire 8. The pulling wire 8 is made of a material which can be cut Alternatively the operation portion 82 can be removed from the pulling wire 8. Therefore by cutting the pulling wire 8 or removing the operation portion 82 from the pulling wire 8, the end of the pulling wire 8 is formed or exposed. By pulling the pulling wire 8, the pulling wire 8 can be separated from the pulling member 15.

The apparatus 30 has also the unlocking mechanism for releasing locking performed by the locking mechanism of the device 12. The unlocking mechanism of the apparatus 30 is constructed of an unlocking shaft 19. The unlocking shaft 19 extends inside the second lumen of the inner tube 7, and penetrates into the third cylindrical part 4 from the distal end of the second passageway 4b of the third cylindrical part 4. The pulling wire 8 is in penetration through the inside of the unlocking shaft 19. To unlock the anchoring portion 17 of the pulling member 15 from the locking portion 43, the pulling wire is pulled to some extent with the distal portion of the unlocking shaft 19 disposed at the rear end (proximal side) of the anchoring portion 17 to decrease the diameter of the anchoring portion 17. Thereafter the unlocking shaft 19 is pressed toward the distal side of the device 12 to some extent Thereby the anchoring portion 17 and the locking portion can be unlocked from each other. The unlocking shaft 19 is removed when there is no need of unlocking the anchoring portion from the locking portion.

Similarly to the embodiment described above with reference to FIGS. 4 and 5, in the device 12 of this embodiment each cylindrical part does not necessarily have to be provided with the connection portion. In this case, it is preferable to form opposed inclined faces at portions of opposed end faces of each cylindrical part, similarly to the above-described embodiment described above with reference to FIGS. 4 and 5.

Figure 8:
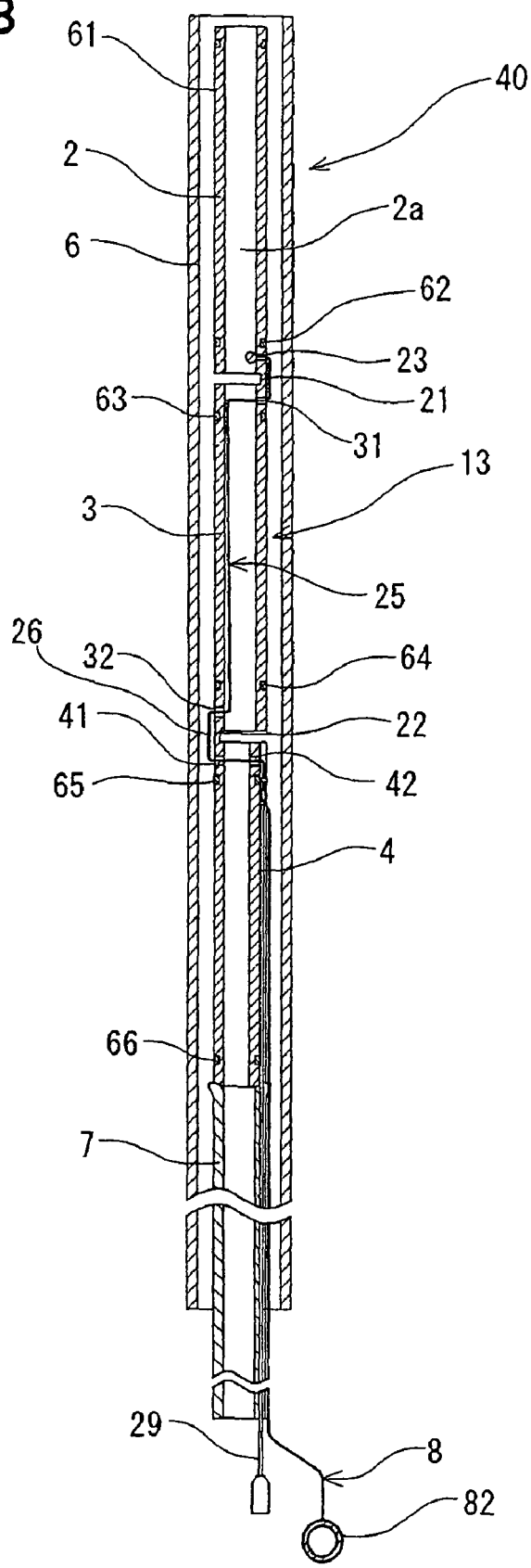
FIG. 8 is a partly omitted enlarged sectional view of another embodiment of an apparatus, for treating the patent foramen ovale, including a device of the present invention for treating the patent foramen ovale.

An embodiment of an apparatus 40 for treating a patent foramen ovale having a device for treating the patent foramen ovale shown in FIG. 8 is described below.

Figure 9:
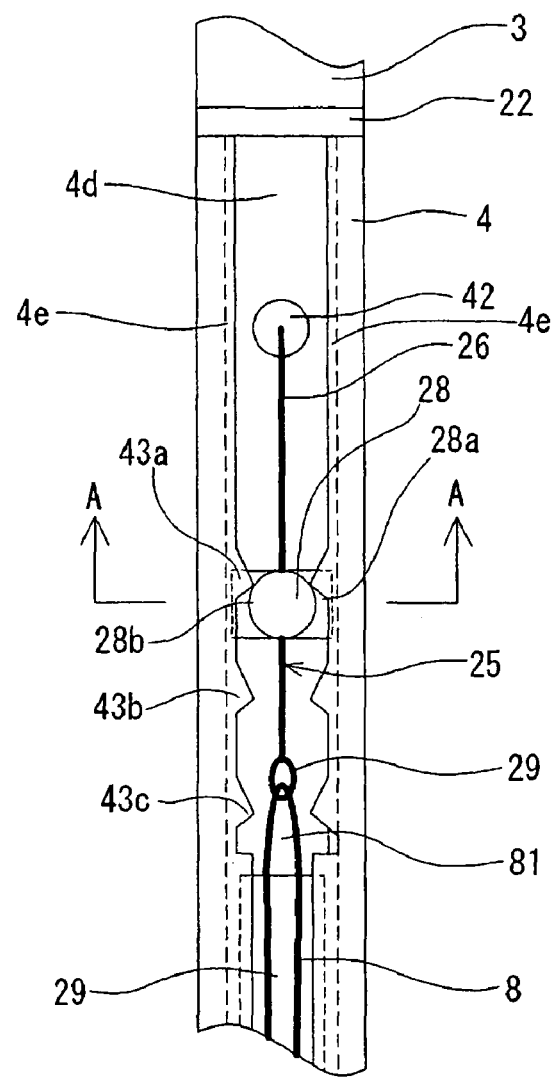
FIG. 9 is a partly enlarged outlook view of the device shown in FIG. 8.
Figure 10:
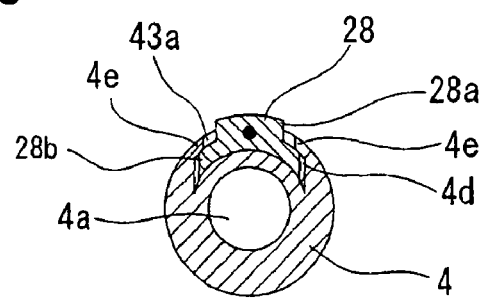
FIG. 10 is a sectional view taken along a line A-A of FIG. 9.

FIG. 8 is a partly omitted enlarged sectional view of another embodiment of an apparatus, for treating the patent foramen ovale, including a device of the present invention for treating the patent foramen ovale. FIG. 9 is a partly enlarged outlook view of the device shown in FIG. 8. FIG. 10 is a sectional view taken along a line A-A of FIG. 9.

A device 13 of the apparatus 40 is different from the device 1 of the apparatus 10 in the configuration of the third cylindrical part 4, the locking mechanism for locking a pulling member 25 including the form of an anchoring member 28 to a locking portion of the third cylindrical part 4, and the unlocking function. The other constructions of the device 13 are similar to those of the device 1 of the above-described embodiment Thus the same parts of this embodiment as those of the above-described embodiment are denoted by the same reference numerals as those of the above-described embodiment, and the above-described descriptions are referred to.

The locking mechanism of the device 40 of the embodiment is constructed of the anchor 28 of the pulling member 25 and a locking portion formed on a groove provided at the side face of the third cylindrical part 4.

In a device 13 of the apparatus 40, as shown in FIGS. 8, 9, and 10, the third cylindrical part 4 has a groove 4d formed on its side face from its distal portion to its proximal end thereof with the groove 4d extending axially. In this embodiment a plurality of locking portions 43a, 43b, and 43c are axially provided on the inner side face of the groove 4d at certain intervals. Each of the locking portions 43a, 43b, and 43c is constructed of a pair of opposed ribs. Each of the locking portions 43a, 43b, and 43c has an inclined face for guiding the anchoring portion 28 that increases in its projected width from its distal side to its proximal side; and an orthogonal face disposed at the rear end portion of the annular inclined face and being orthogonal to the groove. The orthogonal face and the anchoring portion 28 are locked to each other.

The pulling member 25 has a linear portion 26. As in the case of the above-described embodiment the linear portion 26 has a holding portion formed at the distal end thereof to hold the pulling member 25 at the first cylindrical part 2. As shown in FIG. 8, the linear portion 26 of the pulling member 25 extends to the outside from the side hole 23 of the first cylindrical part 2, penetrates into the second cylindrical part 3 from the distal-side side hole 31 of the second cylindrical part 3, extends inside the second cylindrical part 3, extends to the outside from the proximal-side side hole 32 of the second cylindrical part 3, and penetrates into the third cylindrical part 4 from the distal-side side hole 41 of the third cylindrical part 4. The proximal portion of the pulling member 25 (linear portion 26) extends to the outside of the third cylindrical part 4 from the distal-side side hole 42 of the third cylindrical part 4 and penetrates into the groove 4d formed on the side face of the third cylindrical part 4. The anchoring portion 28 is mounted at the proximal end of the pulling member 25 (linear portion 26). An annular portion 29 to be connected to the pulling wire 8 is provided on the anchoring portion 28.

As shown in FIGS. 9 and 10, the groove 4d formed on the side faces of the third cylindrical part 4 has axially extending linear ribs 4e formed on opposed portions of an outer surface of the third cylindrical part 4. As shown in FIGS. 9 and 10, the anchoring portion 28 has a base portion 28a which is slidable inside the groove 4d of the third cylindrical part 4 and is restrained from being separated from the groove 4d by the rib 4e and an anchor-constructing portion 28b formed on the outer surface of the base portion 28a. In this embodiment the anchor-constructing portion 28b is constructed of a rib circularly projected. The anchor-constructing portion 28b does not necessarily have to be circular but may be elliptic or polygonal.

The locking portion 43 to which the anchor-constructing portion 28b of the anchoring portion 28 is locked is formed on the groove 4d of the third cylindrical part 4. In this embodiment, the locking portions 43a, 43b, and 43c are provided at certain intervals along the axial direction of the groove 4d. Each of the locking portions 43a, 43b, and 43c is constructed of opposed ribs. In this embodiment, each of the locking portions 43a, 43b, and 43c is constructed of opposed ribs approximately triangular. The rib constructing the locking portions is formed integrally with the rib 4e. In this embodiment, each of the locking portions 43a, 43b, and 43c has an inclined portion, for guiding the anchor-constructing portion 28b, which inclines in a central direction of the groove from its distal side to its proximal side; and a locking/unlocking-guiding inclined portion which is continuous with the rear end of the annular inclined surface and inclines in the direction of the side face of the groove from its distal side to its proximal side. The locking/unlocking-guiding inclined surface and the anchor-constructing portion 28b are locked to each other.

The pulling wire 8 extends between the inner tube 7 and the outer tube 6. The proximal portion of the pulling wire 8 extends to the outside from the proximal end of the outer tube 6. The pulling wire 8 is separable from the pulling member. More specifically, as shown in FIG. 9, the pulling member 25 of the device 13 has the annular portion 29 at its proximal portion. The pulling wire 8 is folded back after it penetrates through the annular portion 29. That is, the looped portion 81 of the pulling wire 8 is in penetration through the annular portion 29. By pulling the pulling wire 8 (exactly, two wires), the pulling member 25 is pulled to the proximal side of the apparatus 40. The operation portion 82 is mounted at the proximal end (proximal end of two wires) of the pulling wire 8. The pulling wire 8 is made of a material which can be cut Alternatively the operation portion 82 can be removed from the pulling wire 8. Therefore by cutting the pulling wire 8 or removing the operation portion 82 from the pulling wire 8, the end of the pulling wire 8 is formed or exposed. By pulling the pulling wire 8, the pulling wire 8 can be separated from the pulling member 25.

The apparatus 40 has the unlocking mechanism for releasing locking performed by the locking mechanism of the device 13. In the apparatus 40, a groove extending axially is formed on the side face of the inner tube 7 in correspondence with the groove 4d of the third cylindrical part 4. Similarly to the groove 4d, this groove has axially extending linear ribs formed on opposed portions of the outer surface of the inner tube 7. The linear ribs may be composed of dotted ribs. The unlocking mechanism is constructed of the unlocking shaft 29. The unlocking shaft 29 extends through the groove formed on the side face of the inner tube 7 and penetrates into the groove 4d from the proximal portion of the third cylindrical part 4. The distal portion of the unlocking shaft 29 is disposed in the vicinity of the locking portion 43. To unlock the anchoring portion 28 of the pulling member 25 from the locking portion 43, the unlocking shaft 29 is pressed to press the anchoring portion 28 toward the distal side. The unlocking shaft 29 is removed when there is no need of unlocking the anchoring portion 28 from the locking portion 43.

Figure 18:
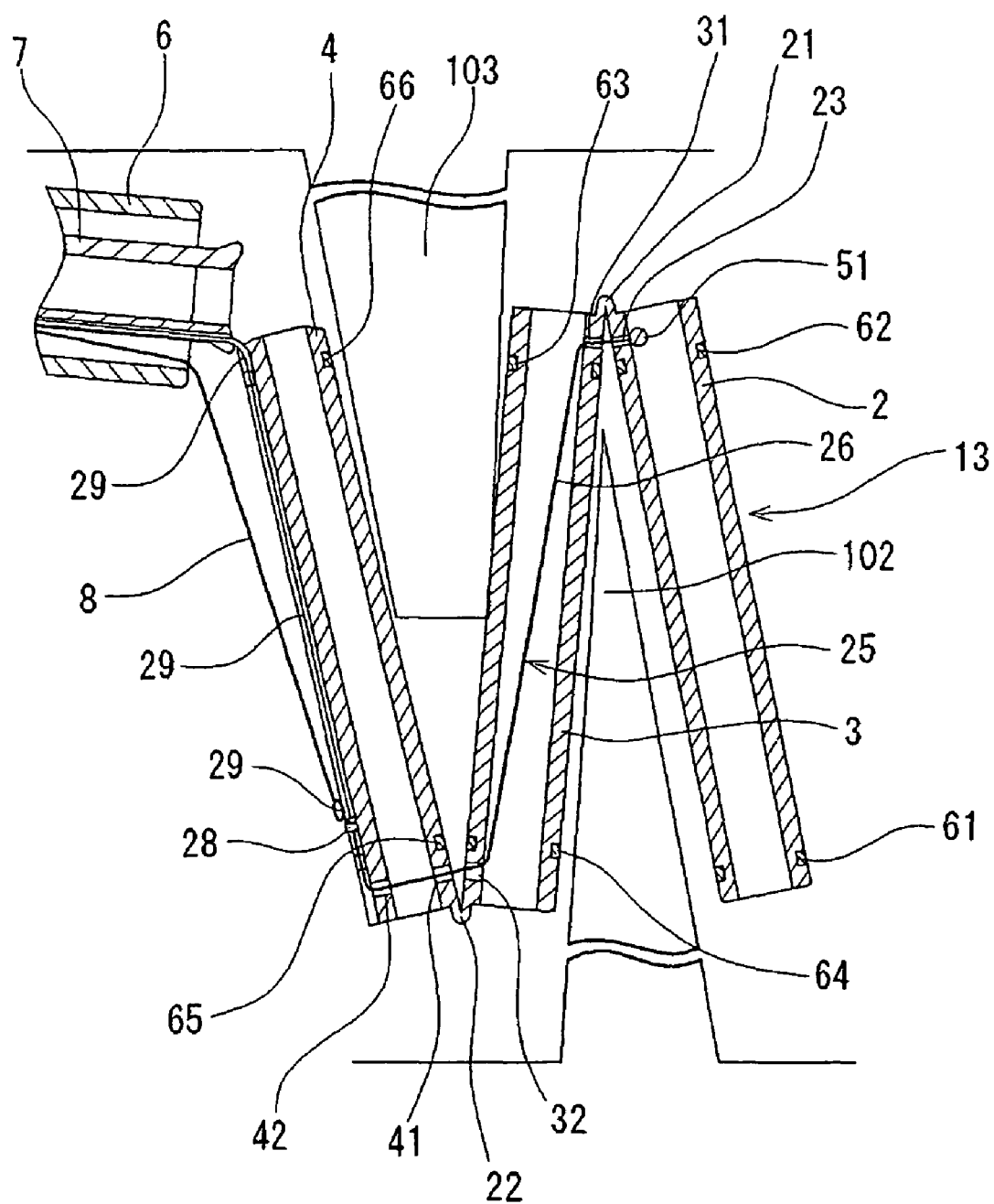
FIG. 18 is an explanatory view for explaining the operation of the apparatus shown in FIGS. 8 through 10.

In the apparatus 40 of this embodiment as shown in FIG. 18, after the device 13 is disposed at the foramen ovale, the pulling member 25 is pulled. Thereby the first connection portion 21 and the second connection portion 22 are bent Consequently the proximal portion of the first cylindrical part 2 and the distal portion of the second cylindrical part 3 become proximate to each other, and the proximal portion of the second cylindrical part 3 and the distal portion of the third cylindrical part 4 become also proximate to each other. As a result, the device 13 deforms into a configuration similar to a letter Z. By further pulling the pulling member 25, the anchoring portion 28 passes through the locking portion 43 (for example, locking portion 43a) and is locked thereto, as shown in FIG. 9. Thereby the device 13 keeps the configuration similar to the letter Z. In this manner, as shown in FIG. 18, the first cylindrical part 2 and the second cylindrical part 3 hold a distal portion 102 of the flap of the septum primum, and the second cylindrical part 3 and the third cylindrical part 4 hold an upper portion 103 of the interatrial septum where the foramen ovale is present Thereby the flap 102 is restrained from opening toward the left atrium of heart.

Similarly to the embodiment described above with reference to FIGS. 4 and 5, in the device 13 of this embodiment, each cylindrical part does not necessarily have to be provided with the connection portion. In this case, it is preferable to form opposed inclined faces at portions of opposed end faces of each cylindrical part, similarly to the above-described embodiment described above with reference to FIGS. 4 and 5.

Figure 11:
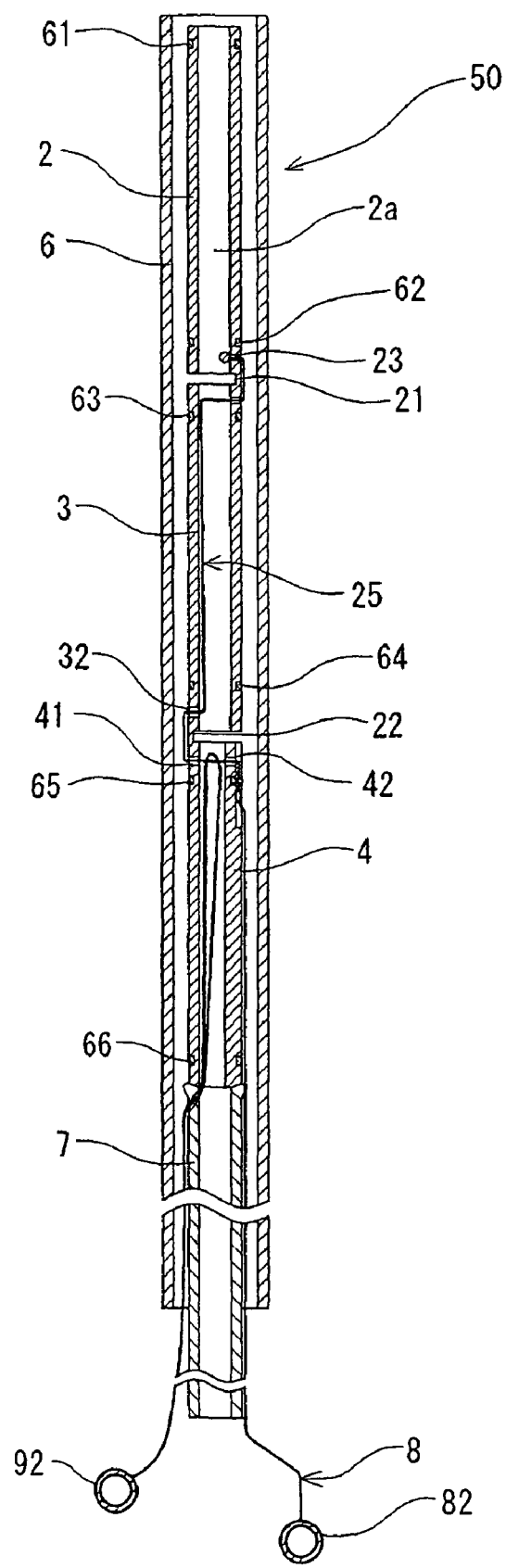
FIG. 11 is a partly omitted enlarged sectional view of another embodiment of an apparatus, for treating the patent foramen ovale, including a device of the present invention for treating the patent foramen ovale.

Like an apparatus 50 shown in FIG. 11, the apparatus having the locking mechanism whose construction is as shown in FIGS. 8 through 10 may have an unlocking mechanism of the apparatus shown in FIGS. 1 through 3. The unlocking mechanism of the apparatus 50 is constructed of the unlocking wire 9 having a loop 91 disposed in the apparatus 50. The pulling member 25 of the device or the pulling wire 8 thereof is in penetration through the loop 91 of the unlocking wire 9. Thus by pulling the unlocking wire 9 toward the proximal side of the device, with the anchoring portion 28 being locked to the locking portion 43, the anchoring portion 28 is forcibly passed through the locking portion 43 and is returned to the distal side of the third cylindrical part 4. Thereby the anchoring portion 53 and the locking side-hole 42 are unlocked from each other. The operation portion 92 is mounted at the proximal end (proximal end of two wires) of the unlocking wire 9. The unlocking wire 9 is made of a material which can be cut Alternatively the operation portion 92 can be removed from the unlocking wire 9. Therefore by cutting the unlocking wire 9 or removing the operation portion 92 from the unlocking wire 9, the end of the unlocking wire 9 is formed or exposed. By pulling the unlocking wire 9, the unlocking wire 9 can be separated from the pulling member or the pulling wire.

The method of using the apparatus having the device of the present invention is described below with reference to FIGS. 12 through 17.

Figure 12:
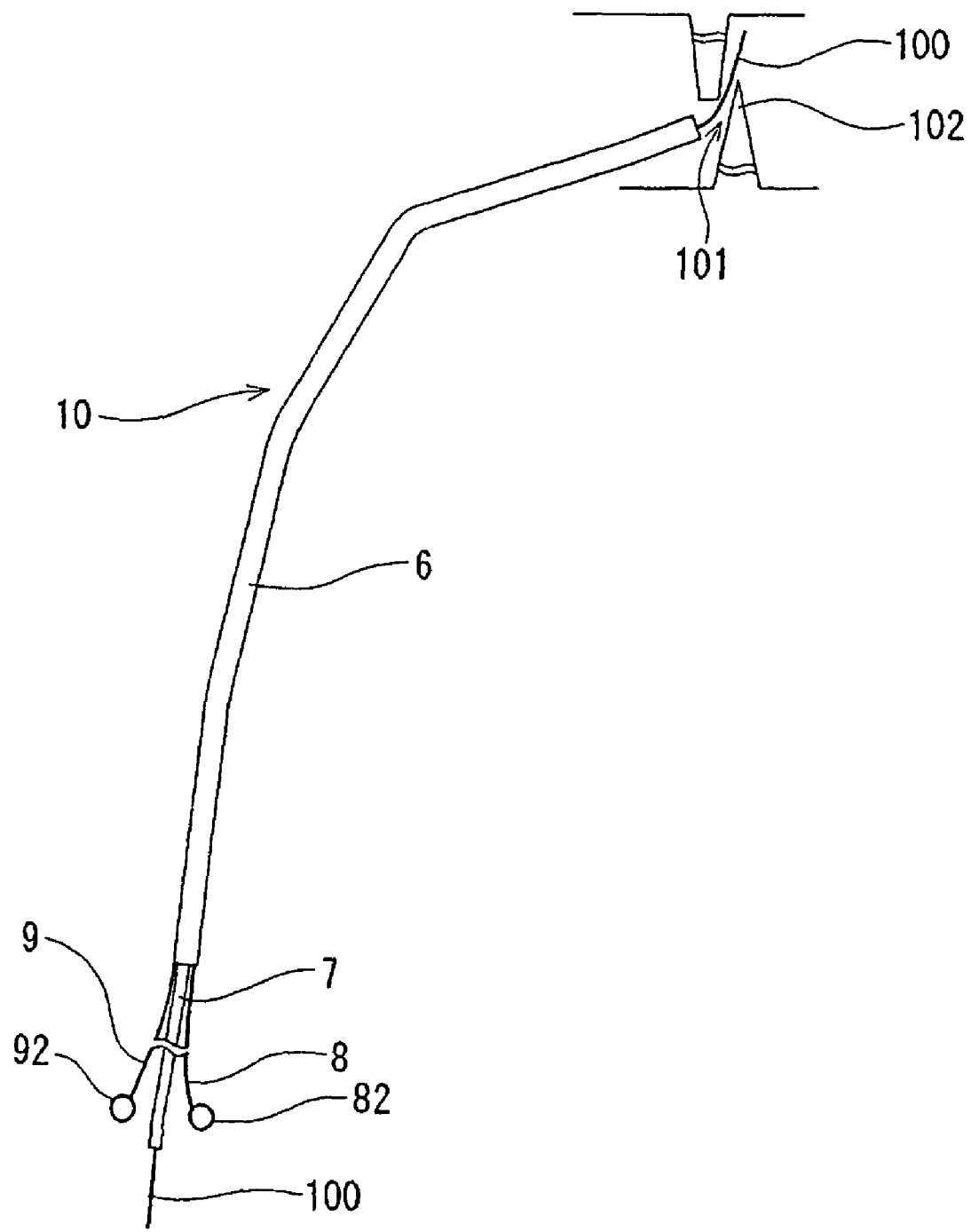
FIG. 12 is an explanatory view for explaining the operation of the apparatus shown in FIGS. 1 through 3.
Figure 13:
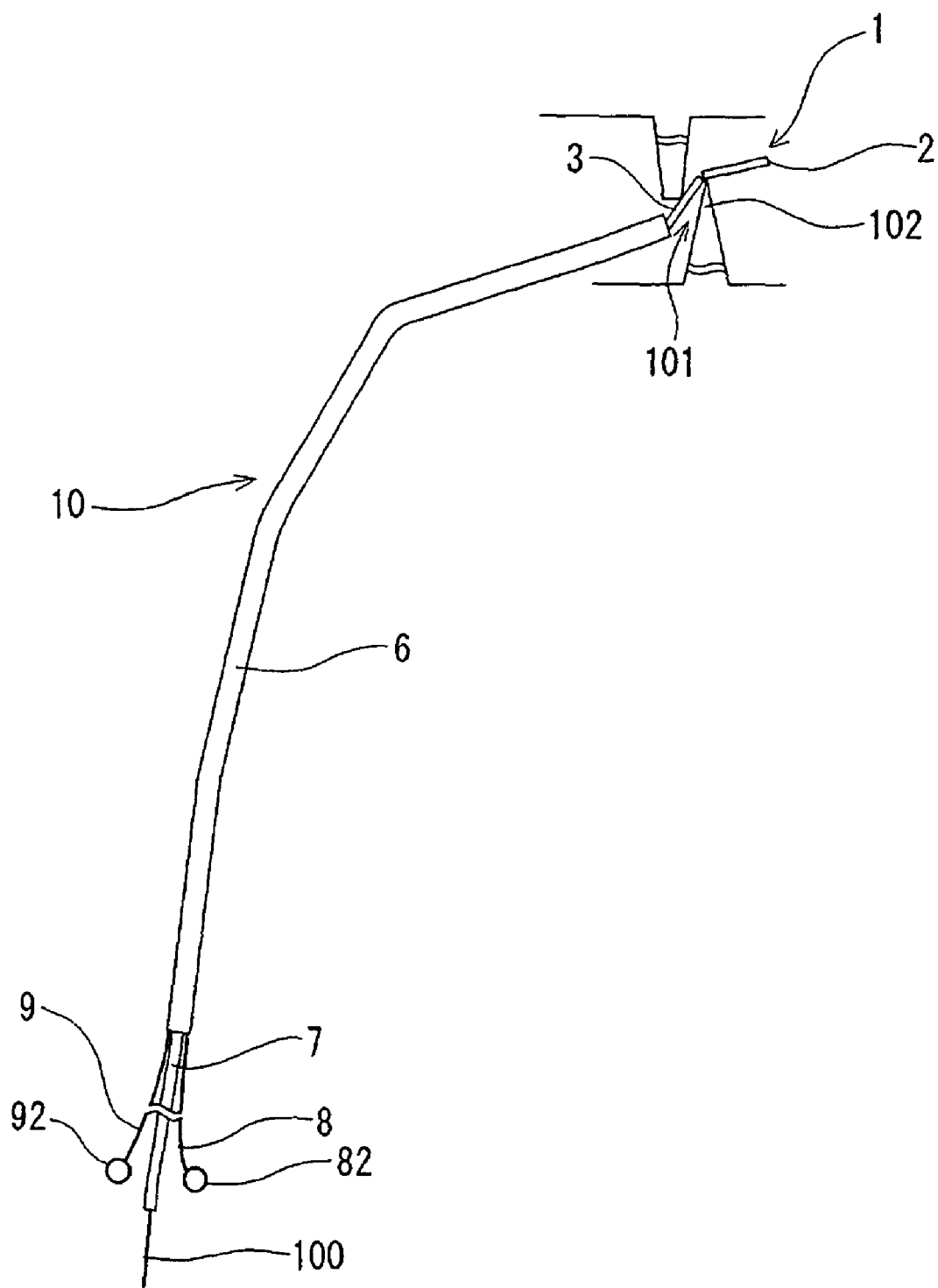
FIG. 13 is an explanatory view for explaining the operation of the apparatus shown in FIGS. 1 through 3.
Figure 14:
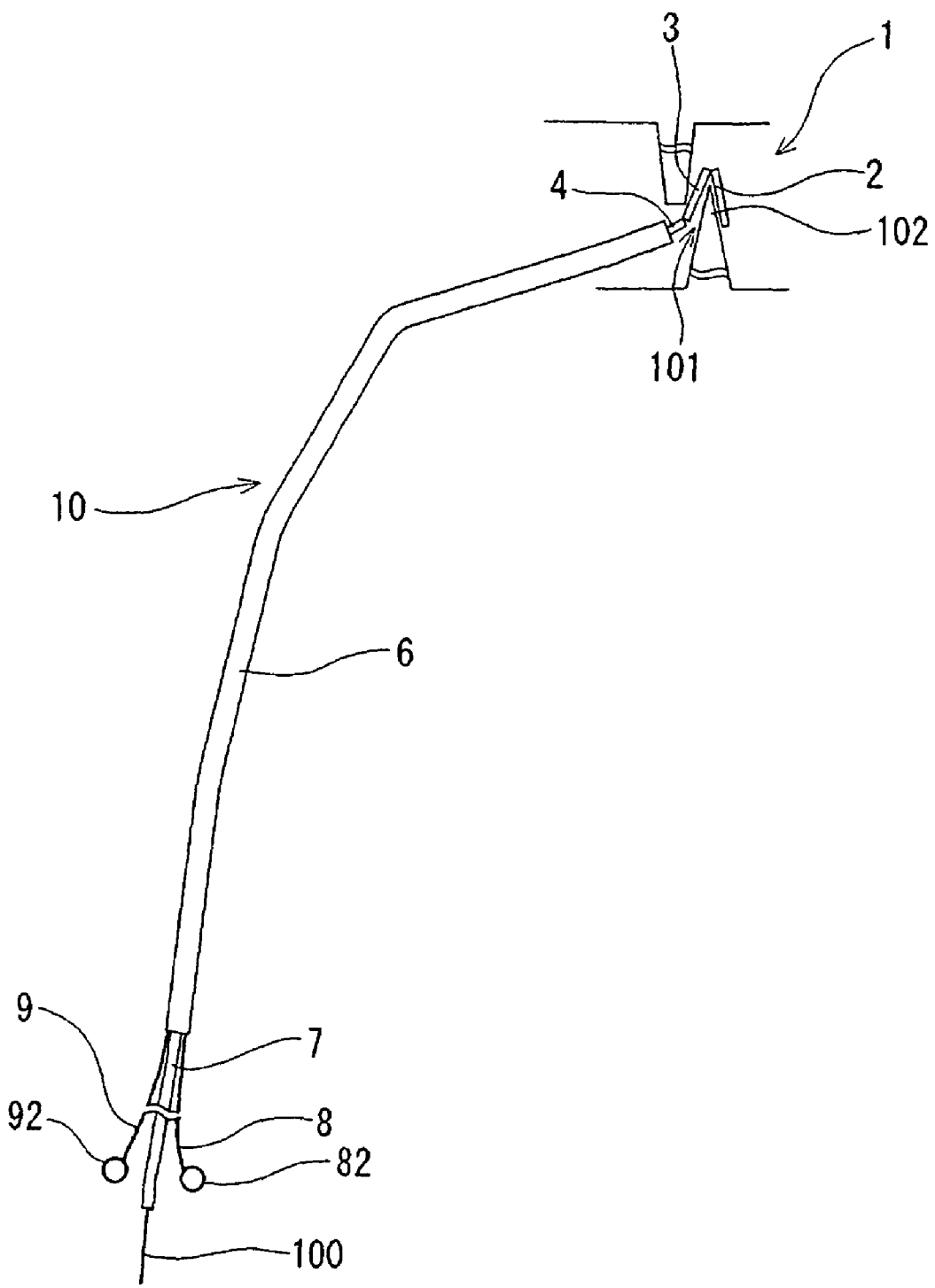
FIG. 14 is an explanatory view for explaining the operation of the apparatus shown in FIGS. 1 through 3.
Figure 15:
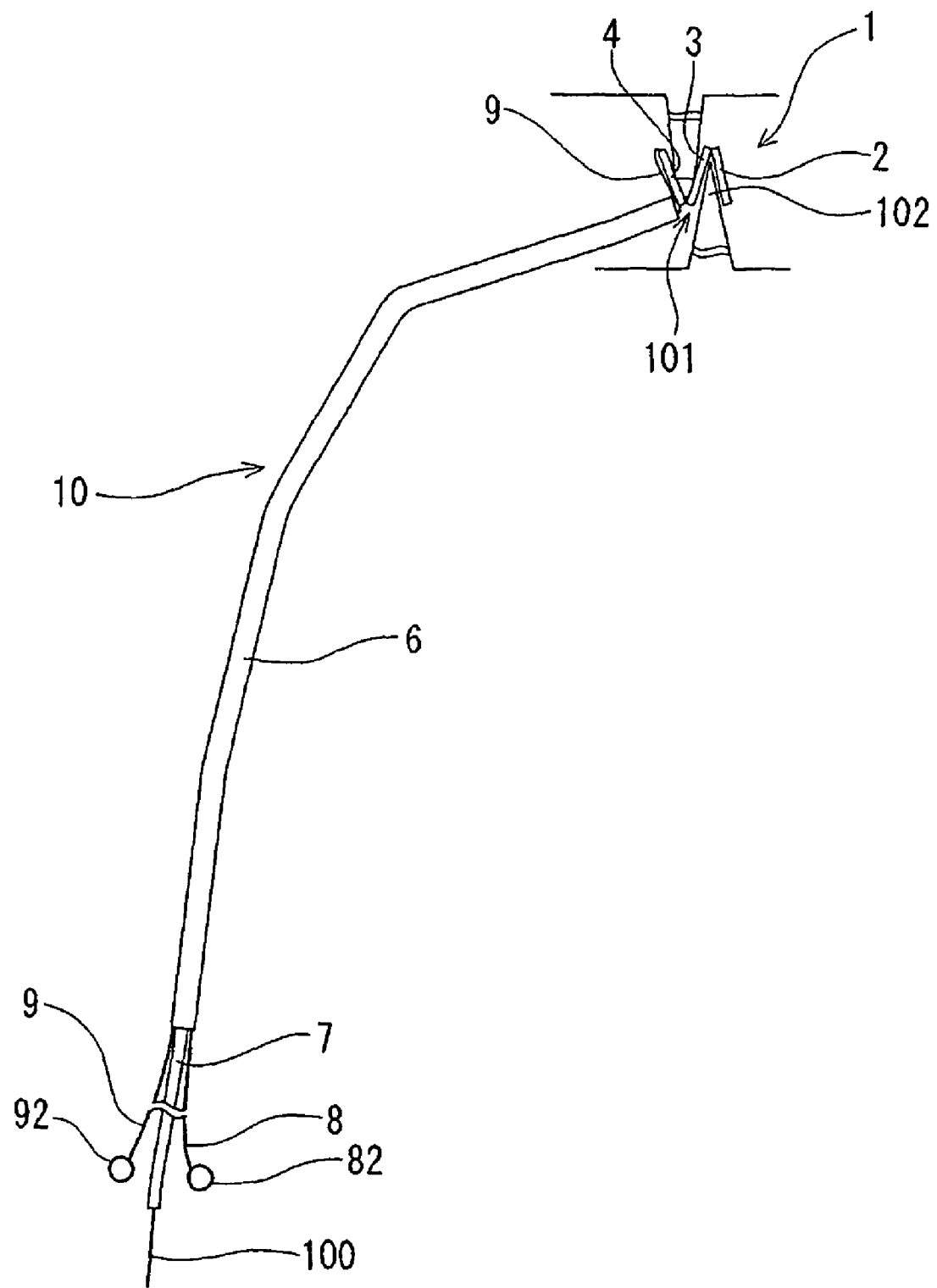
FIG. 15 is an explanatory view for explaining the operation of the apparatus shown in FIGS. 1 through 3.
Figure 16:
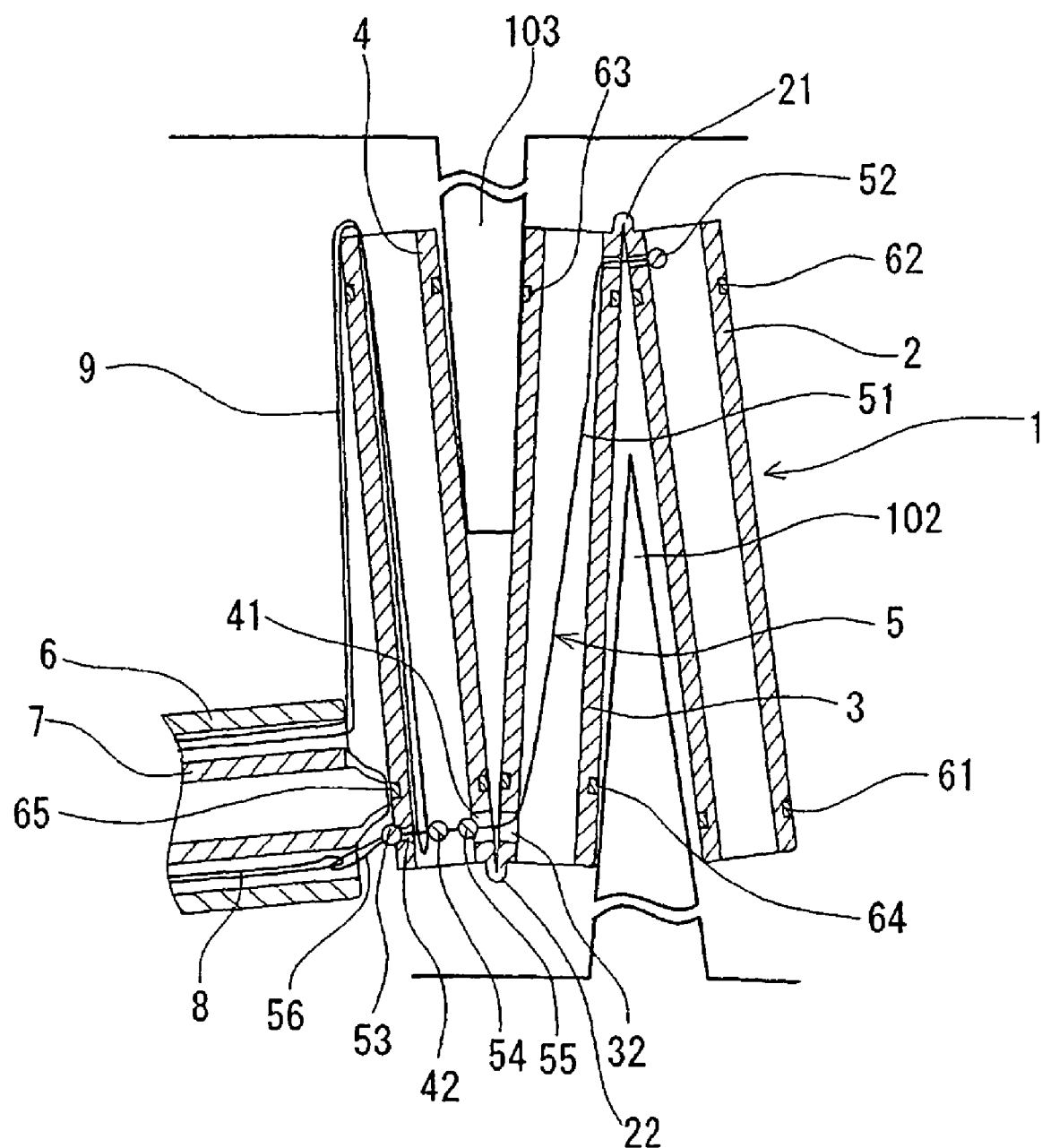
FIG. 16 is an explanatory view for explaining the operation of the apparatus shown in FIGS. 1 through 3.

As shown in FIG. 12, the apparatus 10 is inserted into the femoral vein. Thereafter a guide wire 100 is inserted into the apparatus 10 to insert the apparatus 10 into the lower large vein and the right atrium of heart along the guide wire 100. Then the distal portion of the guide wire 100 is passed through a foramen ovale 101 of the interatrial septum. Thereafter as shown in FIG. 13, the device 1 is pressed out of the distal end of the outer tube 6 of the apparatus 10 along the guide wire 100 to dispose the first cylindrical part 2 at the left atrium of heart with respect to the septum primum and dispose the second cylindrical part 3 at the foramen ovale. Then with the inner tube 7 maintained at its original position, the outer tube 6 is pulled toward its proximal side to expose the third cylindrical part 4 inside the right atrium of heart as shown in FIG. 14. After the entire device 1 is exposed in the heart the pulling wire 8 is pulled. As a result as shown in FIG. 15, the proximal portion of the first cylindrical part 2 and the distal portion of the second cylindrical part 3 become proximate to each other, and the proximal portion of the second cylindrical part 3 and the distal portion of the third cylindrical part 4 become also proximate to each other. Consequently the device 1 deforms into a configuration similar to the letter Z. More specifically describing, as shown in FIG. 16, by pulling the pulling wire 8 toward the proximal side of the apparatus 10, the pulling member 5 is pulled. Thereby the first connection portion 21 and the second connection portion 22 are bent Consequently the proximal portion of the first cylindrical part 2 and the distal portion of the second cylindrical part 3 become proximate to each other, and the proximal portion of the second cylindrical part 3 and the distal portion of the third cylindrical part 4 become also proximate to each other. As a result, the device 1 deforms into the configuration similar to the letter Z. By keeping pulling the pulling member 8, the anchoring portion 53 passes through the locking side-hole 42 and is locked thereto, as shown in FIG. 16. Thereby the device 1 keeps the deformed configuration similar to the letter Z. In this manner, the first cylindrical part 2 and the second cylindrical part 3 hold a distal portion 102 of the flap of the septum primum, and the second cylindrical part 3 and the third cylindrical part 4 hold an upper portion 103 of the interatrial septum where the foramen ovale is present Thereby the flap 102 is restrained from opening toward the left atrium of heart When the operator desires to decrease the distance between the distal portion of the first cylindrical part 2 and the proximal portion of the second cylindrical part 3 and the distance between the distal portion of the second cylindrical part 3 and the proximal portion of the third cylindrical part 4, the pulling wire 8 is pulled further. Thereby the anchoring portions 54 and 55 pass through the locking side-hole 42 and are locked thereto. Thereby the device 1 keeps the deformed configuration similar to the letter Z.

Figure 17:
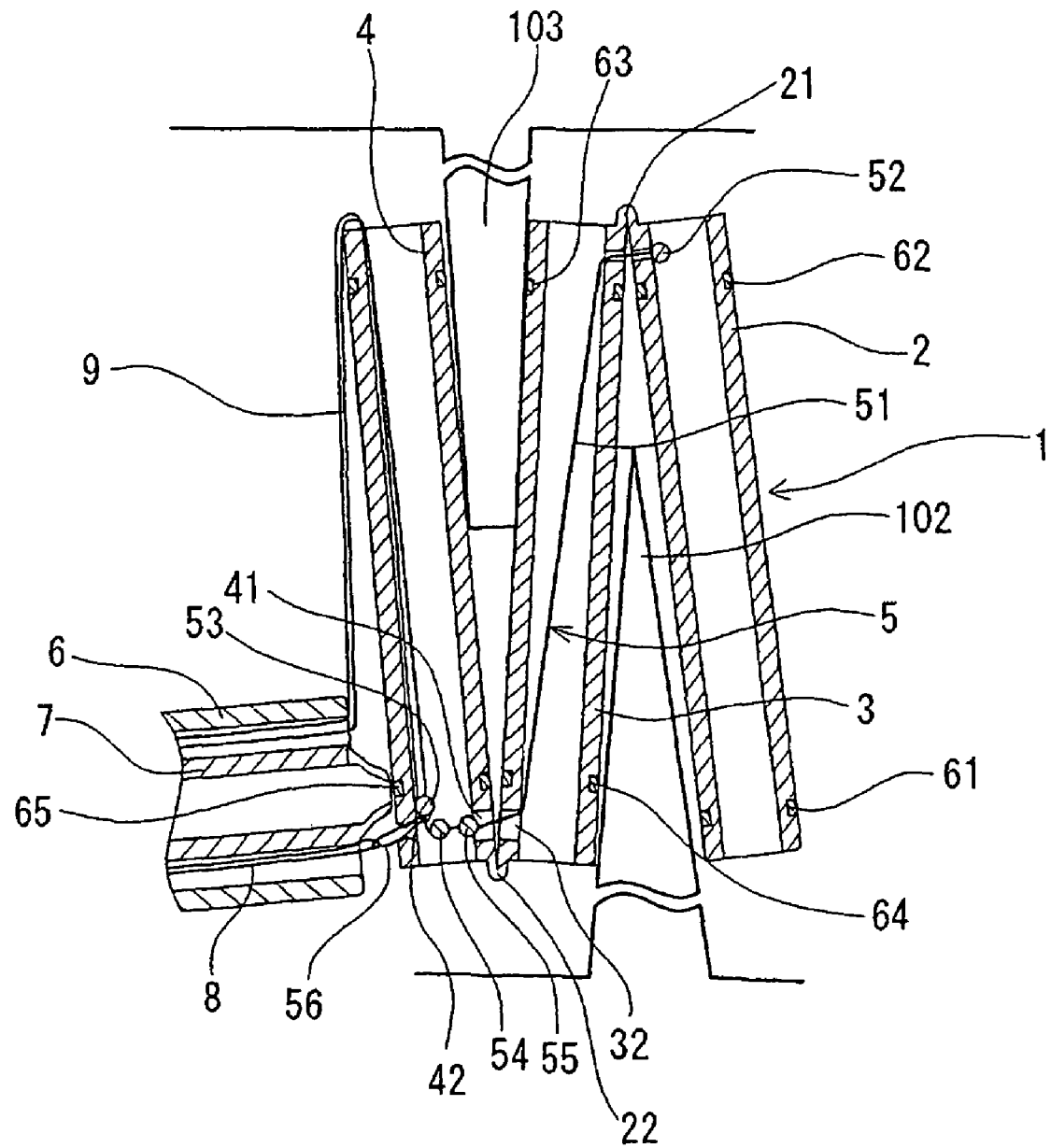
FIG. 17 is an explanatory view for explaining the operation of the apparatus shown in FIGS. 1 through 3.

When the anchoring portion (for example, the anchoring portion 53) is desired to be unlocked from the locking side-hole 42, the unlocking wire 9 is pulled to the proximal side of the apparatus 10. Thereby as shown in FIG. 17, the proximal portion of the pulling member 5 is pulled toward the third cylindrical part 4, and the anchoring portion (for example, the anchoring portion 53) passes through the locking side-hole 42, thus penetrating into the third cylindrical part 4. Thereby both are unlocked from each other.

When an object is achieved because the anchoring portion 53 has been locked to the locking side-hole 42 and because the deformed state of the device 1 similar to the letter Z has been obtained, the pulling wire 8 is cut at a position outward from the proximal end of the apparatus 10 and pulled out. The unlocking wire 9 is also cut at a position outward from the proximal end of the apparatus 10 and pulled out Thereafter the apparatus 10 (outer tube 6 and inner tube 7) is pulled out of the organism, together with the guide wire 100.

The device of the present invention for treating the patent foramen ovale has the first part having the predetermined length; the second part having the predetermined length; the third part having the predetermined length; and the pulling member whose proximal end penetrates into the second part from the side face of the distal portion of the second part crosses the second cylindrical part obliquely and extends from the side face of the proximal portion of the second part and penetrates or is penetrable into the third part from the side face of the distal portion of the third part with the distal end of the pulling member held by the proximal portion of the first part A part of the locking mechanism provided at the proximal portion of the pulling member and a part of the locking mechanism provided at the third part are locked to each other, when the pulling member is pulled to allow the first part and the second part to be proximate to each other and the second part and the third part to be proximate to each other.

By pulling the pulling member, the proximal portion of the first cylindrical part and the distal portion of the second cylindrical part become proximate to each other, and the proximal portion of the second cylindrical part and the distal portion of the third cylindrical part become also proximate to each other. As a result the device deforms into the configuration similar to the letter Z. The locking mechanism maintains the configuration. In this manner, the first cylindrical part and the second cylindrical part hold the distal portion of the flap of the septum primum, and the second cylindrical part and the third cylindrical part hold the upper portion of the interatrial septum where the foramen ovale is present Thereby the flap is restrained from opening toward the left atrium of heart, and blood is prevented from flowing from the right atrium of heart to the left atrium of heart in spite of the patent foramen ovale. In the device of the present invention, a spring action is not utilized, but the straight members are mechanically bent or folded to hold the distal end of the flap of the septum primum and the open portion of the foramen ovale. Therefore they are little damaged and a load is applied little thereto.

A device and an apparatus of another embodiment of the present invention for treating the patent foramen ovale are described below with reference to the drawings.

Figure 19:
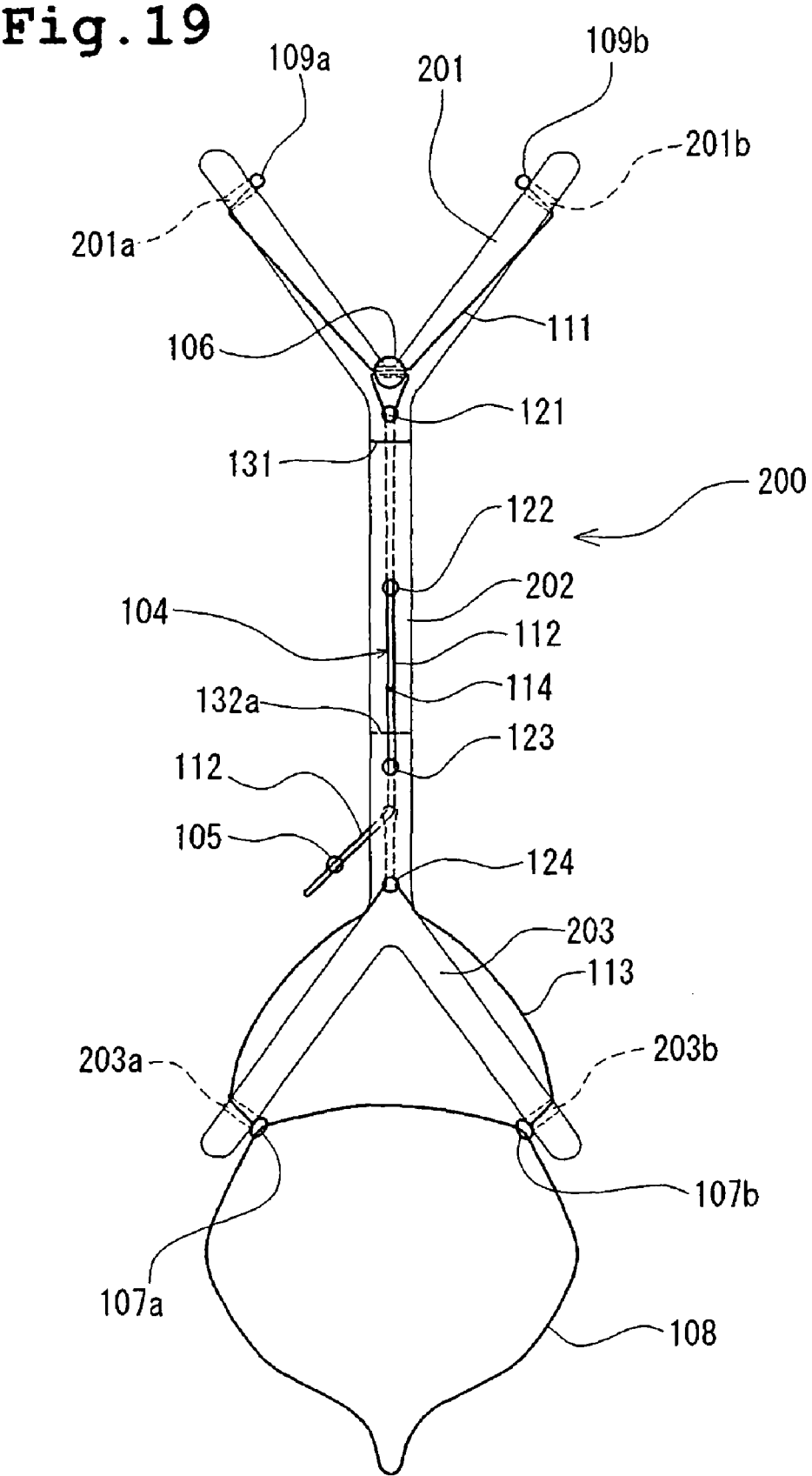
FIG. 19 is a front view of a device of another embodiment of the present invention for treating the patent foramen ovale.
Figure 20:
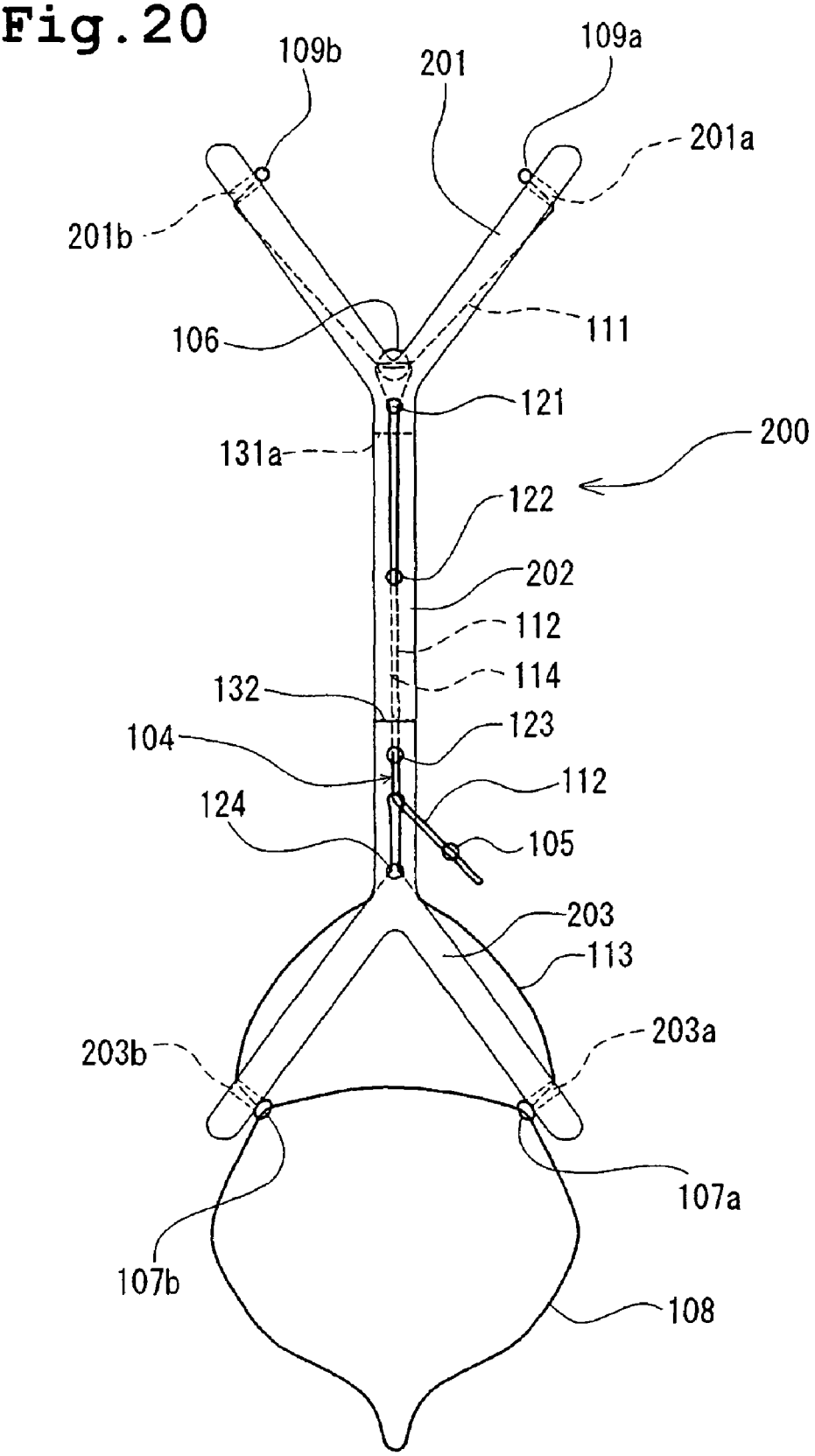
FIG. 20 is a rear view of the device shown in FIG. 19.
Figure 21:
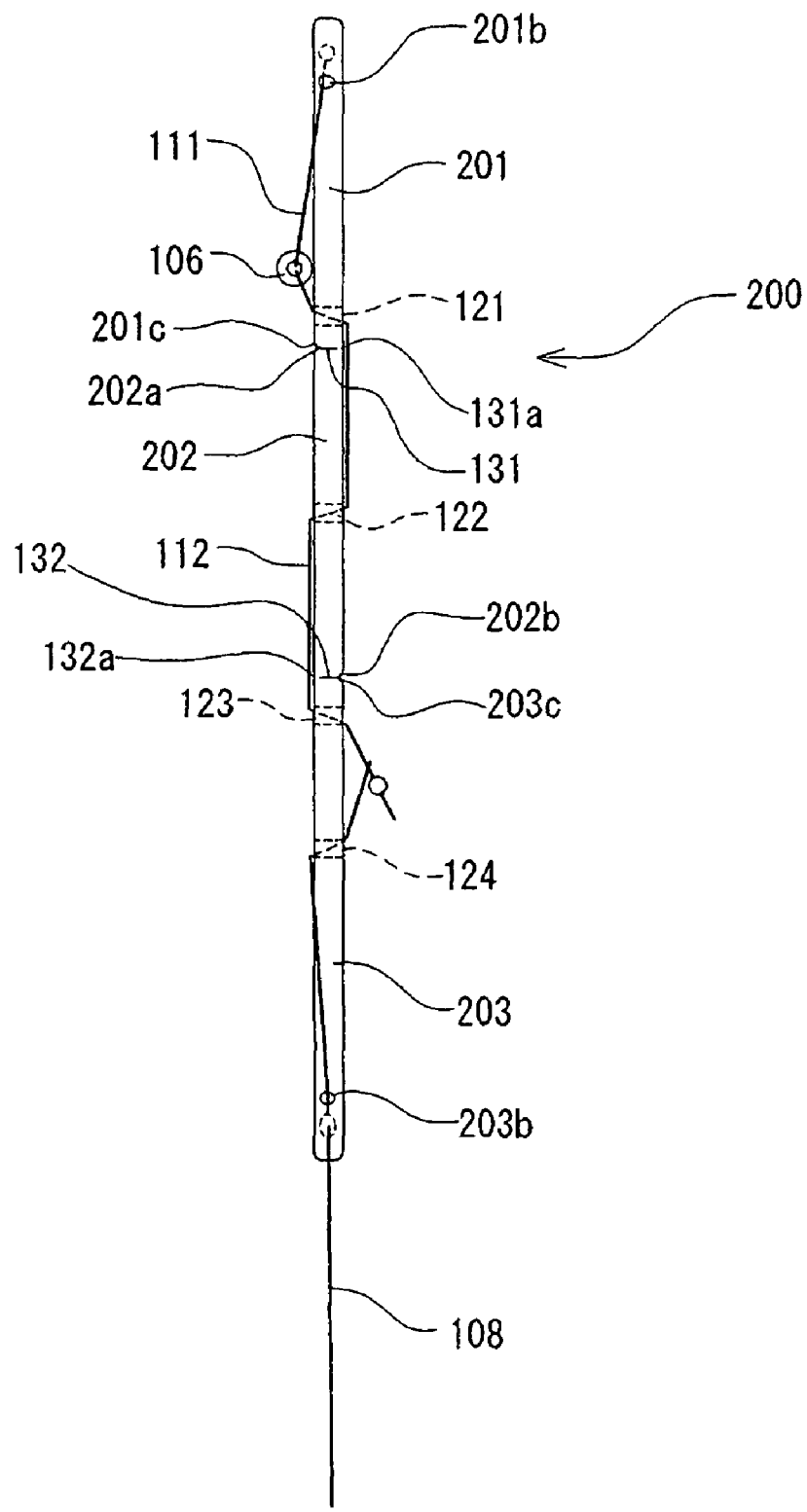
FIG. 21 is a right side view of the device shown in FIG. 19.
Figure 22:
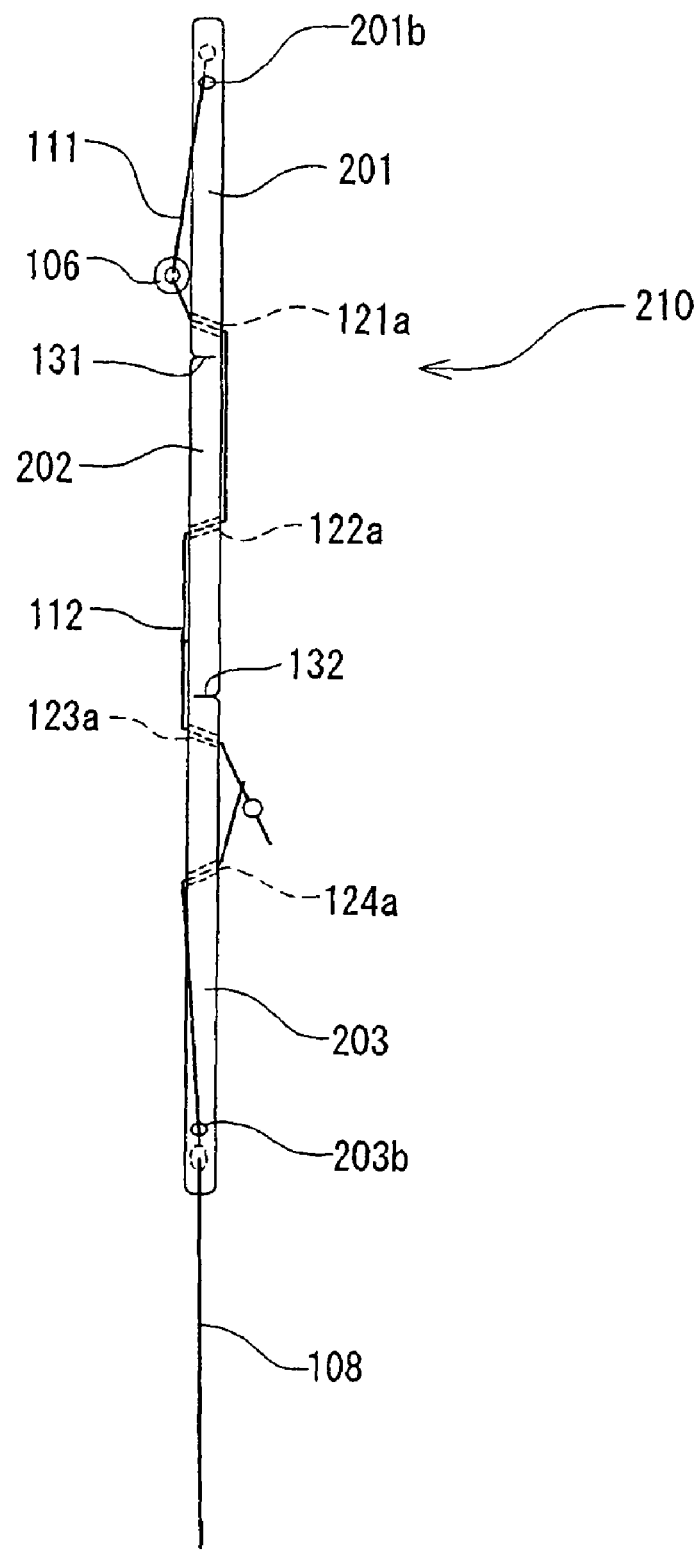
FIG. 22 is a side view of a device of another embodiment of the present invention for treating the patent foramen ovale.
Figure 26:
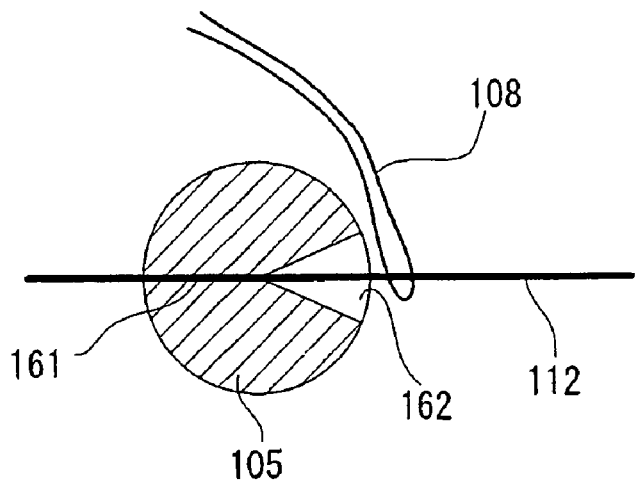
FIG. 26 is an explanatory view for explaining an example of a deformed state holding member of the device of the present invention for treating the patent foramen ovale.
Figure 27:
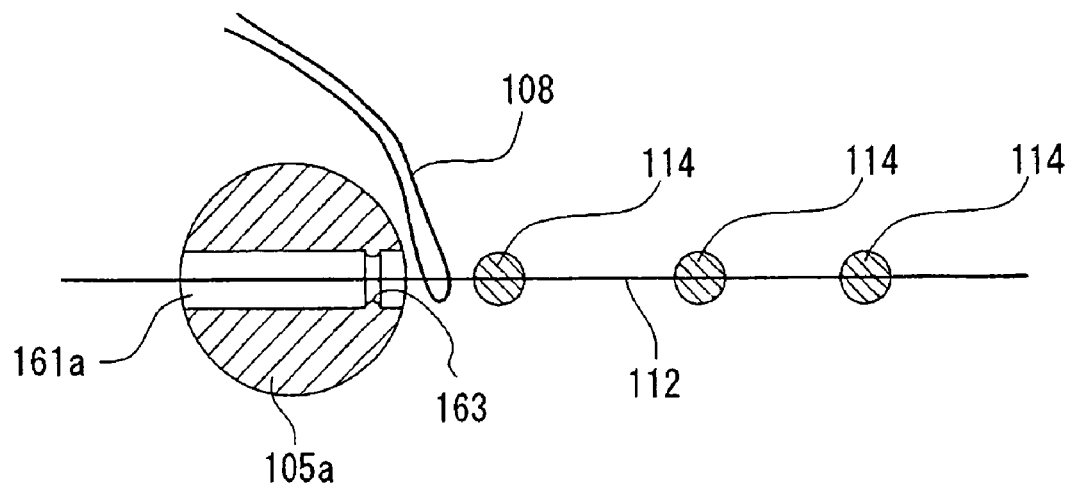
FIG. 27 is an explanatory view for explaining another example of the deformed state holding member of the device of the present invention for treating the patent foramen ovale.

FIG. 19 is a front view of a device of another embodiment of the present invention for treating the patent foramen ovale. FIG. 20 is a rear view of the device shown in FIG. 19. FIG. 21 is a right side view of the device shown in FIG. 19. FIG. 22 is a side view of a device of another embodiment of the present invention for treating the patent foramen ovale. FIG. 26 is an explanatory view for explaining an example of a deformed state holding member of the device of the present invention for treating the patent foramen ovale. FIG. 27 is an explanatory view for explaining another example of the deformed state holding member of the device of the present invention for treating the patent foramen ovale.

A device 200 of this embodiment for treating the patent foramen ovale is used to treat the foramen ovale formed on the septum in the organism. As shown in FIGS. 19 through 21 and 25, the device 200 includes a first part 201 having a predetermined length and a through-passageway 121 provided at a proximal side thereof; a second part 202 having a predetermined length and a through-passageway 122; a third part 203 having a predetermined length and a through-passageway 123 provided at a distal side thereof; a pulling member 104, one end of which is held by the first part 201 and which is extended sequentially in penetration through the through-passageway 121 of the first part 201, the through-passageway 122 of the second part 202, and the through-passageway 123 of the third part 203; and a deformed state holding member 105, provided at other side of the pulling member 104, for holding the device 200 deformed into an approximately Z configuration, in a side view, which is formed by approach or contact of a side face of a proximal portion of the first part 201 to or with a side face of a distal portion of the second part 202 at one side thereof and approach or contact of a side face of a proximal portion of the second part 202 at other side thereof to or with a side face of a distal portion of the third part 203 owing to pulling of the pulling member 104.

An apparatus 110 of this embodiment for treating the patent foramen ovale has an outer tube 140, the device 200, an inner tube 141, and a pulling wire 148.

In the device 200 of this embodiment the second part 202 can be bent at the proximal portion of the first part 201, and the third part 203 can be bent at the proximal portion of the second part 202. Although the above-described construction is preferable in this embodiment, the first part, the second part, and the third part may be separate like the device 1 of the above-described embodiment More specifically, as shown in the drawings, the device 200 of this embodiment has an integrally formed body member having the first part 201, the second part 202, and the third part 203. The body member has a first connection portion 131a bendably connecting the first part 201 and the second part 202 with each other and a second connection portion 132a bendably connecting the second part 202 and the third part 203 with each other.

It is preferable that the first part 201 branches with two branched portions spread out toward its distal side and that the two branched portions can be approached to each other. More specifically, as shown in FIG. 19, the first part 201 branches at a portion of its proximal side to form a shape similar to that of a letter "Y". The branched portion of the first part 201 is made of an elastically deformable material. Thereby the first part 201 can be accommodated in the outer tube 140 with the two branched portions proximate to each other. After the first part 201 is discharged from the outer tube 140, it is capable of returning to the original shape similar to that of the letter "Y". The first part 201 may be entirely made of the elastically deformable material or only the branched portion may be made of the elastically deformable material. Instead of making the branched portion of the elastically deformable material, the branched portion may be opened and closed mechanically.

Similarly to the first part 201, it is preferable that the third part 203 branches with two branched portions spread out toward its proximal side and that the two branched portions can be approached to each other. More specifically, as shown in FIG. 19, the third part 203 branches at a portion of its distal side to form a shape similar to that of the inverted letter "Y". The branched portion of the third part 203 is made of the elastically deformable material. Thereby the third part 203 can be accommodated in the outer tube 140 with the two branched portions proximate to each other. After the third part 203 is discharged from the outer tube 140, it is capable of returning to the original shape similar to that of the inverted latter "Y". The third part 203 may be entirely made of the elastically deformable material or only the branched portion may be made of the elastically deformable material. Instead of making the branched portion of the elastically deformable material, the branched portion may be opened and closed mechanically.

As shown in FIG. 19 and 21, the device 200 of this embodiment has a slit 131 forming a boundary between the first part 201 and the second part 202. As shown in FIGS. 19 and 21, the slit 131 is extended from a front surface of the device 200 toward a rear surface thereof and does not reach the rear surface thereof. Therefore a slit-unformed position of the slit-formed portion constructs a connection portion 131a connecting the first part 201 and the second part 202 with each other. Similarly, as shown in FIGS. 20 and 21, a slit 132 is extended from the rear surface of the device 200 toward the front surface thereof and does not reach the front surface thereof. Therefore the slit-unformed position of the slit-formed portion constructs a connection portion 132a connecting the second part 202 and the third part 203 with each other.

Figure 25:
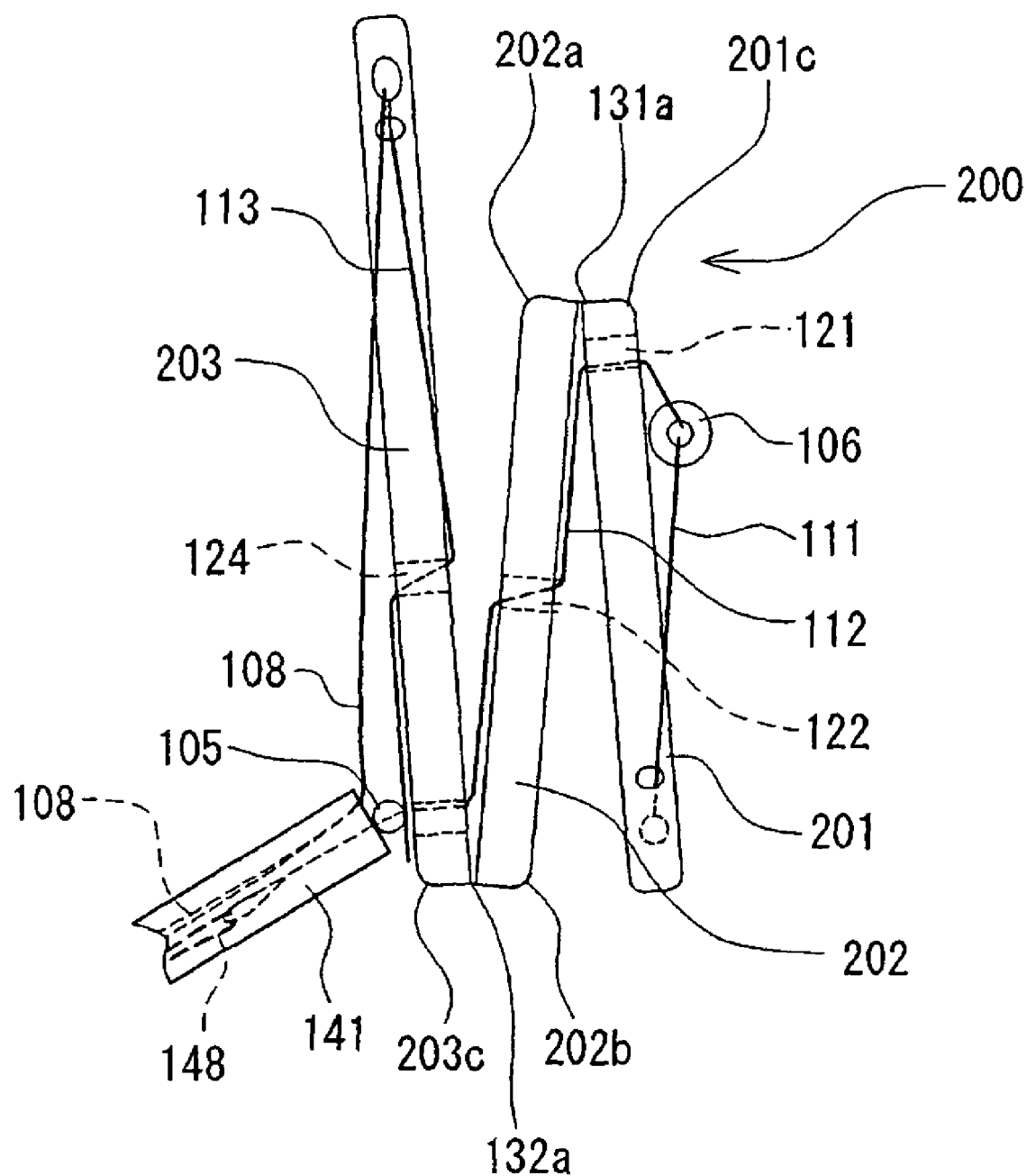
FIG. 25 is an explanatory view for explaining the operation of the apparatus shown in FIGS. 23 and 24.

Therefore as shown in FIG. 25, in the device 200 of this embodiment, by pulling the pulling member 104, the first part 201 bends about the second part 202 at the slit 131, and the third part 203 bends about the second part 202 at the slit 132 in a direction opposite to the bent direction of the first part 201. As a result, the device 200 forms a shape similar to that of a letter "N" in a side view. The device 200 may be so constructed that when the device 200 is bent, the first part may be fractured from the second part and that the third part may be fractured from the second part In this case, the connection portion is not formed.

As shown in FIGS. 21 and 25, it is preferable to chamfer a corner 201c of the portion in which the slit 131 is formed (the corner of the portion in which the slit 131 of the first part 201 is formed) and a corner 202a (the corner of the portion in which the slit 131 of the second part 202 is formed) confronting the corner 201c. It is also preferable to chamfer a corner 202b of the portion in which the slit 132 is formed (the corner of the portion in which the slit 132 of the second part 202 is formed) and a corner 203c (the corner of the portion in which the slit 132 of the third part 203 is formed) confronting the corner 202b. Thereby as shown in FIG. 25, the exposed corners are not edged when the pulling member is pulled. Thus it is possible to restrain the device 200 from damaging an inner wall of the organism.

In this embodiment, the first part 201, the second part 202, and the third part 203 are pillar-shaped. Although it is preferable that they are pillar-shaped, they may be cylindrical like the first part 201, the second part 202, and the third part 203 of the above-described embodiment.

It is preferable that the through-passageway 122 of the second part 202 is disposed at the central side of the second part 202 in its longitudinal direction.

The pulling member 104 is held at its one end by the first part 201 and extended sequentially through the through-passageway 121 of the first part 201, the through-passageway 122 of the second part 202, and the through-passageway 123 of the third part 203.

In this embodiment, one end of the pulling member 104 is held by the first part 201 at its distal portion. In this embodiment, the pulling member 104 is constructed of a first pulling member 111 held at the distal portion of each of the two branched portions of the first part 201, and a second pulling member 112 which is capable of pulling the proximal side of the first pulling member 111 and extended sequentially in penetration through the through-passageway 121 of the first part 201, the through-passageway 122 of the second part 202, and the through-passageway 123 of the third part 203.

The first pulling member 111 is a linear wire having two distal portions each of which is held by the distal portion of the each of the two branched portions of the first part 201. This construction allows the branched configuration of the first part 201 to be securely accomplished by pulling the first pulling member 111. In this embodiment, distal portions of the first pulling member 111 penetrate through holes 201a, 201b respectively formed at distal portions of the first part 201. Anchoring portions 109a, 109b are fixed to the distal portions of the first pulling member 111 respectively. Thereby each distal portion of the first pulling member 111 is held by the first part 201.

The second pulling member 112 is a looped linear wire. The looped distal portion of the second pulling member 112 is positioned in proximity to the proximal portion of the first part and the first pulling member 111, penetrates through the through-passageway 121 of the first part 201, is extended to the proximal side of the second part 202 along the rear surface of the device, penetrates through the through-passageway 122 of the second part 202, appears on the front surface of the device, penetrates through the through-passageway 123 of the third part 203, and is extended to the rear surface of the device.

The proximal side of the first pulling member 111 can be pulled by pulling the second pulling member 112. The pulling member 104 has a linking member 106 linking the first pulling member 111 and the second pulling member 112 with each other. As the linking member 106, a material having a through-passageway through which the first pulling member 111 and the second pulling member 112 penetrate is used.

More specifically, the linking member 106 is composed of a bead member having a through-passageway. The linking member 106 may be composed of members having any configurations cylindrical, ring-shaped, and the like provided that they have a through-passageway. Instead of providing the pulling member 104 with the linking member, the first pulling member 111 and the second pulling member 112 may be intersected with each other at the proximal portion of the first pulling member 111 or the first pulling member 111 and the second pulling member 112 may be joined with each other at the proximal portion of the first pulling member 111.

The pulling member 104 may be composed of one member instead of being composed of the first pulling member 111 and the second pulling member 112

It is preferable that in this embodiment, as shown in FIG. 19, the third part 203 has a second through-passageway 124 disposed at the proximal side thereof with respect to the through-passageway 123 formed at the distal side of the third part 203. It is preferable that the device 200 has a linear wire 113 for said third part having a distal-side portion looped at a portion, of said pulling member, which is disposed between the through-passageway 123 of the third part 203 and the deformed state holding member and a proximal side portion which penetrates through the second through-passageway 124 of the third part 203 and is held at a proximal portion of the third part 203. The pulling member 104 (the second pulling member 112) may be so constructed that the two linear wires constructing the pulling member 104 pass through the looped distal portion of the linear wire 113 for the third part 203 or only one of the two linear wires constructing the pulling member 104 (the second pulling member 112) passes through the looped distal portion of the linear wire 113 for the third part 203. In this embodiment the proximal portions of the linear wire 113 for the third part penetrate through holes 203a, 203b respectively formed at the proximal portions of the third part 203. Anchoring portions 107a, 107b are fixed to the proximal portions of the linear wire 113 for the third part respectively. Thereby each distal portion of the linear wire 113 for the third part is held by the third part 203. A ring-shaped member is used for the anchoring portions 107a, 107b.

This construction allows the linear wire 113 for the third part to be pulled when the deformed state holding member 105 which is described later is operated. Thereby the branched configuration of the third part 203 can be securely accomplished.

As shown in FIG. 26, it is preferable that the deformed state holding member 105 has a through-passageway 161 through which the pulling member (the second pulling member 112) can be slidably penetrated at a predetermined resistance. That is, the deformed state holding member 105 is capable of sliding along the second pulling member 112 by being pressed rearward or forward at a degree of force higher than the predetermined degree of force. In a normal state, the deformed state holding member 105 is not moved because it is subjected to the fictional resistance of the pulling member and that of the inner surface of the through-passageway. It is preferable that the through-hole 161 has a diameter-enlarged portion 162 into which the pulling member is inserted. It is preferable that the deformed state holding member 105 is composed of a sphere.

As shown in FIG. 27, the device 200 may have an anchoring portion 114 provided at the other side (proximal side) of the pulling member 104 (the second pulling member 112). A deformed state holding member 105a may have a through-hole 161a through which the pulling member 104 (the second pulling member 112) penetrates and a locking portion 163 capable of locking the anchoring portion 114 thereto so that the pulling member is capable of sliding through the through-hole 161*a*. In this embodiment the second pulling member 112 slides through the through-passageway 161*a* without being subjected to a resistance. In this embodiment the locking portion 163 is constructed of an annular rib formed inside the through-hole 161*a*. The anchoring portion 114 is composed of a sphere. The anchoring portion 114 has an outer diameter a little larger than a minimum inner diameter of the annular rib 163. The anchoring portion 114 and the locking portion (annular rib) 163 are locked to each other, when the pulling member (second pulling member 112) is pulled and the anchoring portion 114 rides across the annular rib 163. Thereby the anchoring portion 114 is restrained from moving to the distal side of the anchoring portion 114, and a deformed state of the device is maintained. As shown in FIG. 27, it is preferable to form a plurality of the anchoring portions 114. Thereby the deformed state of the device can be selected.

The first part 201, the second part 202, and the third part 203 of the device 20 may be circular, elliptic, polygonal, and the like in the sectional configuration thereof. The width and outer diameter of the material for forming each of the first part 201, the second part 202, and the third part 203 is favorably in the range of 0.1 to 5.0 mm and more favorably in the range of 1.0 to 3.0 mm. Tie longitudinal length of the first part 201 is favorably in the range of 5 to 50 mm. The longitudinal length of the second part 202 is favorably in the range of 5 to 50 mm. The longitudinal length of the third part 203 is favorably in the range of 5 to 50 mm. The distance between the distal ends of the branched portions of the first part 201 is favorably in the range of 10 to 40 mm. The distance between the proximal ends of the branched portions of the third part 203 is favorably in the range of 10 to 40 mm. In the device 200 of this embodiment, the longitudinal length of the third part 203 is set larger than that of the first part and that of the second part Thereby the flap of the septum primum can be held securely. It is preferable that the longitudinal length of the third part 203 is set longer than that of the second part.

As the material for forming each part (first part, second part, and third part) of the device, in consideration of flexibility, hardness, strength, sliding property, kink resistance, and stretching property, it is preferable to selectively use polymers such as polyethylene, polypropylene, nylon, polyethylene terephthalate, fluorine-containing polymers (for example, PTFE, ETFE); and thermoplastic elastomers. The thermoplastic elastomer is used selectively from synthetic resin of nylon family (for example, polyamide elastomer), urethane family (for example, polyurethane elastomer), polyester family (for example, polyethylene terephthalate elastomer), and olefin family (for example, polyethylene elastomer, polypropylene elastomer). As described above, it is preferable that the branched portion of the first part 201 and that of the third part 203 are made of an elastically deformable material. As the elastically deformable material, the above-described resins can be used. The thermoplastic elastomer is most favorable. In the device, by using a two-color molding method, the branched portion of the first part 201 and that of the third part 203 of the body member may be made of the above-described elastomer, and the other parts may be made of resin compatible with the elastomer and having a hardness than that of the elastomer by using a two-color molding method. Although it is preferable that the branched portion of the first part 201 and that of the third part 203 are made of the elastically deformable material, the branched portions may be made of a plastically deformable material because when the first pulling member and the linear wire for the third part are pulled, the branched portion of the first part 201 and that of the third part 203 are restored to the original configuration thereof similar to that of Y.

It is preferable to treat the inner surface of the through-passageway of each of the first, second, and third parts to enhance the sliding property of the pulling member. As such treatment, it is possible to adopt a method of applying or fixing the following hydrophilic polymers to the inner surface thereof: poly(2-hydroxyethyl methacrylate), polyhydroxyethyl acrylate, hydroxypropyl cellulose, methyl vinyl ether-maleic anhydride copolymer, polyethylene glycol, polyacryl amide, and polyvinyl pyrrolidone. To enhance the sliding property of the inner surface of the outer tube and/or the outer surface of the inner tube, these hydrophilic polymers may be applied or fixed thereto.

As the material for forming the linear portion of the pulling member and the linear wire for the third part, it is possible to use metals such as stainless steel, Ni—Ti alloy, Cu—Zn alloy, Ni—Al alloy, tungsten, tungsten alloy, titanium, titanium alloy, cobalt alloy, tantalum; comparatively rigid polymeric materials such as polyamide, polyimide, ultra-high-molecular-weight polyethylene, polypropylene, fluororesin; and a combination of these materials. As the linear portion 111, 112, 113, a wire or a plurality of twisted wires can be preferably used. Although not specifically limited, the diameter of the linear portion is favorably in the range from 0.01 mm to 1.3 mm and more favorably in the range from 0.1 mm to 0.3 mm.

Like a device 210 shown in FIG. 22, a through-hole formed in penetration through the first part 201, second part 202, and the third part 203 may be formed obliquely to reduce a resistance to the movement of the pulling member in the pulling direction. More specifically, a through-hole 121*a* of the first part 201 is formed obliquely toward the proximal side of the first part 201 from the front surface of the body member of the device 210 to the rear surface thereof. A through-hole 122*a* of the second part 202 is formed obliquely toward the proximal side of the second part 202 from the rear surface of the body member of the device 210 to the front surface thereof. A through-hole 123*a* of the third part 203 is formed obliquely toward the proximal side of the third part 203 from the front surface of the body member of the device 210 to the rear surface thereof. A second through-hole 124*a* of the third part 203 is formed obliquely toward the proximal side of the third part 203 from the rear surface of the body member of the device 210 to the front surface thereof.

An apparatus for treating the patent foramen ovale of another embodiment of the present invention is described below with reference to FIGS. 23 through 25.

Figure 23:
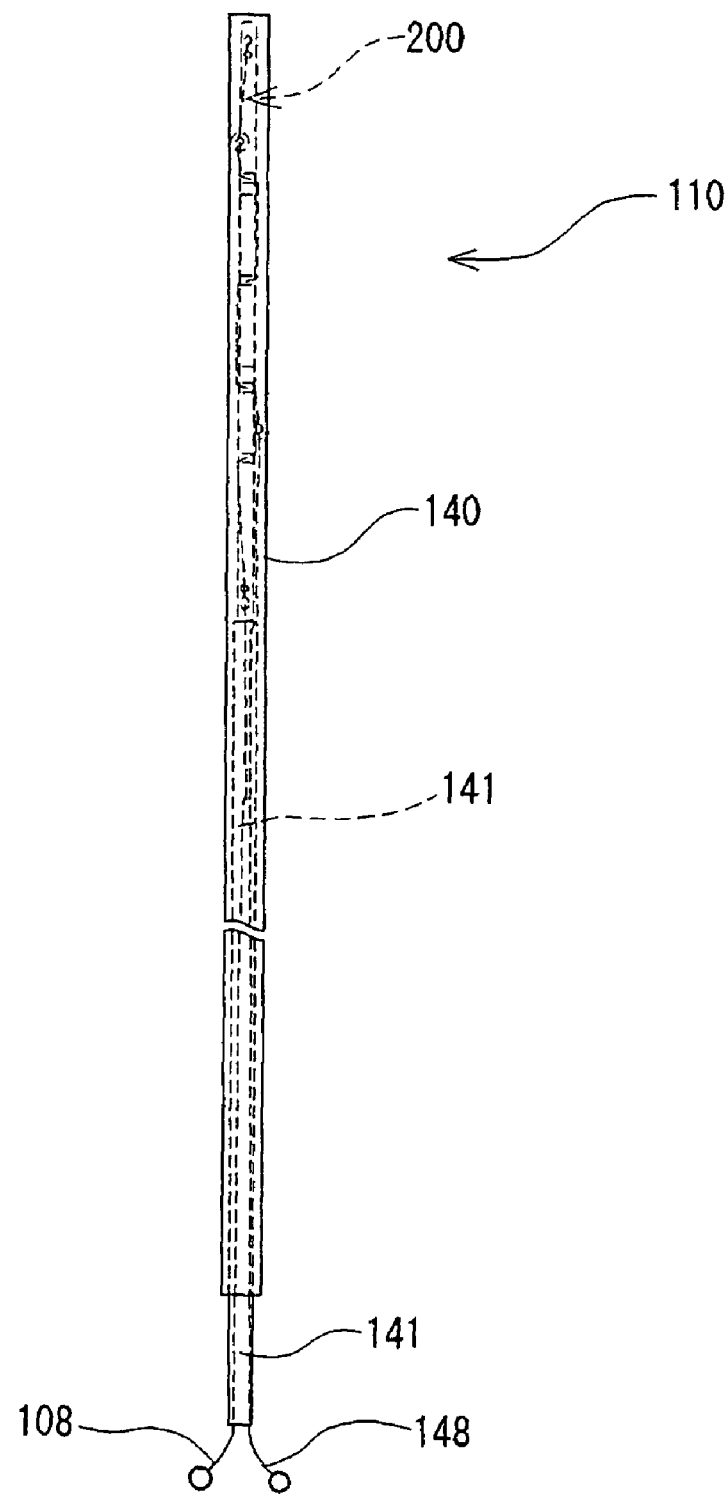
FIG. 23 shows an outlook of the apparatus having the device of the present invention for treating the patent foramen ovale shown in FIG. 19.

FIG. 23 shows an outlook of the apparatus having the device shown in FIG. 19. FIG. 24 is a partly omitted enlarged sectional view of the apparatus shown in FIG. 23. FIG. 25 is an explanatory view for explaining the operation of the apparatus shown in FIGS. 23 and 24.

The apparatus 110 of this embodiment for treating the patent foramen ovale is used to treat the foramen ovale formed on the septum in the organism. As shown in FIGS. 23 and 24, the apparatus 110 has an outer tube 140, the device 200 accommodated inside a distal portion of the outer tube 140 with the device 200 kept almost straight, an inner tube 141 for pressing the device 200 out of the distal end of the outer tube 140 and operating the deformed state holding member 105, and the pulling wire 148 which is capable of pulling the pulling member 104 and separable from the pulling member 104.

Figure 24:
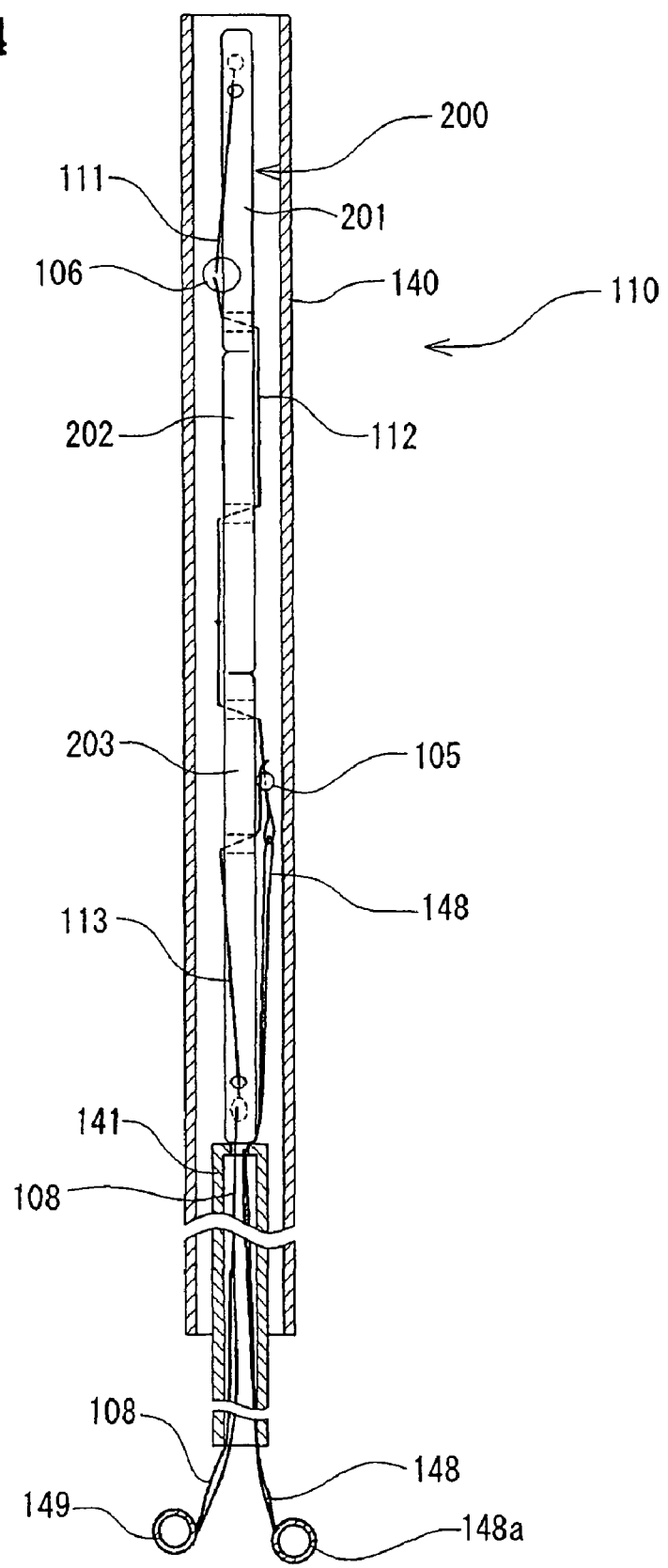
FIG. 24 is a partly omitted enlarged sectional view of the apparatus shown in FIG. 23.

As shown in FIGS. 23 and 24, the outer tube 140 is tubular. The outer tube 140 is open at its distal and proximal ends. The opening formed at the distal end of the outer tube 140 functions as a release opening when the device 200 is retained in a foramen ovale. The distal portion of the outer tube 140 serves as an accommodation portion for accommodating the device 200 therein when the device 200 is straight.

The outer diameter of the outer tube 140 is favorably in the range from 0.3 mm to 7.0 mm and more favorably in the range from 1.2 mm to 5.0 mm. The inner diameter of the outer tube 140 is favorably in the range from 0.2 mm to 6.5 mm. The length of the outer tube 140 is favorably in the range from 300 mm to 2000 mm and more favorably in the range from 700 mm to 1500 mm.

As shown in FIGS. 23 and 24, the inner tube 141 is tubular. The inner tube 141 is open at its distal and proximal ends. The inner tube 141 is accommodated in the outer tube 140. The distal portion of the inner tube 141 is capable of contacting the proximal portion of the device 200. Thus the inner tube 141 is capable of pressing the device 200 from the distal end of the outer tube 140. As shown in FIG. 24, in the apparatus 110 of this embodiment, the distal portion of the inner tube 141 contacts the deformed state holding member 105 and the deformed state holding member 105 to be operated. The apparatus 110 has a pulled state release member for releasing a deformation state held by the deformed state holding member 105 of the device 200.

The outer diameter of the inner tube 141 is favorably in the range from 0.1 mm to 5.0 mm and more favorably in the range from 1.0 mm to 3.0 mm. The inner diameter of the inner tube 141 is favorably in the range from 0.05 mm to 4.8 mm. The length of the inner tube 141 is favorably in the range from 300 mm to 2000 mm and more favorably in the range from 700 mm to 1500 mm.

As the material for forming the outer tube 140 and the inner tube 141, in consideration of properties (flexibility, hardness, strength, sliding property, kink resistance, and stretching property) demanded for them, it is preferable to selectively use polymers such as polyethylene, polypropylene, nylon, polyethylene terephthalate, fluorine-containing polymers (for example, PTFE, ETFE); and thermoplastic elastomers. The thermoplastic elastomer includes synthetic resin of nylon family (for example, polyamide elastomer), urethane family (for example, polyurethane elastomer), polyester family (for example, polyethylene terephthalate elastomer), olefin family (for example, polyethylene elastomer, polypropylene elastomer).

It is preferable to treat the outer surface of the outer tube 140 to enhance the sliding property thereof. As such treatment it is possible to adopt a method of applying or fixing the following hydrophilic polymers to the inner surface thereof: poly(2-hydroxyethyl methacrylate), polyhydroxyethyl acrylate, hydroxypropyl cellulose, methyl vinyl ether-maleic anhydride copolymer, polyethylene glycol, polyacryl amide, and polyvinyl pyrrolidone. To enhance the sliding property of the inner surface of the outer tube and/or the outer surface of the inner tube, these hydrophilic polymers may be applied or fixed thereto.

The pulling wire 148 is folded back after it penetrates through a looped portion or an annular portion formed at the proximal portion of the pulling member 104 (the second pulling member 112) of the device 200. In this embodiment, as shown in FIG. 24, the distal portion of the pulling wire 148 is folded back inside the outer tube 140 after it penetrates through the looped portion or the annular portion formed at the proximal portion of the second pulling member 112 and is then penetrated into the inner tube 141 from the opening disposed at the distal end of the inner tube 141. Thereafter the distal portion of the pulling wire 148 is exposed to the outside from the proximal end of the inner tube 141. That is, the pulling wire 148 is extended to its proximal side with two wires kept in parallel after it (one wire) is folded back at its distal portion. By pulling the pulling wire 148 (exactly, two wires), the pulling member 104 (the second pilling member 112) is pulled to the proximal side of the device 200. An operation portion 148a is mounted at the proximal end (proximal end of two wires) of the pulling wire 148. The pulling wire 148 is made of a material which can be cut Alternatively the operation portion 148a can be removed from the pulling wire 148. Therefore by cutting the pulling wire 148 or removing the operation portion 148a from the pulling wire 148, the end of the pulling wire 148 is formed or exposed. By pulling the pulling wire 148, the pulling wire 148 can be separated from the pulling member 104. An annular portion may be formed on the proximal end of the pulling member 112 by mounting an annular member thereon instead of forming the looped portion thereon.

The apparatus 110 of this embodiment has a pulled state release member 108 which is pulled to move the deformed state holding member 105 to the other side (proximal side) of the pulling member 104.

The device 200 of the apparatus 110 of this embodiment has the second through-passageway 124 disposed at the proximal side of the third part 203 with respect to the through-passageway 123 formed at the distal side of the third part 203, and the distal-side portion looped at the portion, of the pulling member 104, which is disposed between the through-passageway 123 of the third part 203 and the deformed state holding member 105. The device 200 further includes the linear wire 113, for the third part 203, which penetrates through the second through-passageway 124 of the third part 203 and has the proximal side portion held by the third part 203 at the proximal portion thereof. The pulled state release member 108 is constructed of a linear wire for pulling a portion, of the linear wire 113 for the third part, which is held by the third part 203 at the proximal portion thereof.

More specifically, as described above, in the device 110 of this embodiment, the third part 203 is provided with the linear wire 113. The proximal portions of the linear wire 113 for the third part penetrate through the holes 203a, 203b respectively formed at the proximal portions of the third part 203. The anchoring portions 107a, 107b are fixed to end portions of the linear wire 113 for the third part respectively. The ring-shaped member is used for the anchoring portions 107a, 107b. The linear wire 113 for the third part extends to the distal side of the device 200 in penetration through the second through-passageway 124 of the third part 203. The distal portion of the linear wire 113 for the third part loops at the portion, of the pulling member 104, which is disposed between the through-passageway 123 of the third part 203 and the deformed state holding member 105.

In the apparatus 110 of this embodiment, the pulled state release member 108 is composed of the looped wire (pulled state release wire) penetrating through the ring-shaped anchoring portions 107a, 107b of the linear wire 113 for the third part.

More specifically, the pulled state release wire 108 is folded back after it penetrates through the ring-shaped anchoring portions 107a, 107b of the linear wire 113 for the third part of the device 200. As shown in FIG. 19, in this embodiment the pulled state release wire 108 is folded back at its distal portion after it penetrates through the ring-shaped anchoring portions 107a, 107b and is then penetrated into the inner tube 141 from the opening disposed at the distal end thereof. Thereafter the pulled state release wire 108 is exposed to the outside from the proximal end of the inner tube 141. That is, the pulled state release wire 108 is extended to its proximal side with two wires kept in parallel after it (one wire) is folded back at its distal portion. By pulling the pulled state release wire 108 (exactly, two wires), the linear wire 113 for the third part is pulled. Thereby the deformed state holding member 105 can be moved to the proximal side of the pulling member 104 (second pulling member 112) by means of the looped distal portion of the linear wire 113 for the third part Owing to the movement of the deformed state holding member 105 to the proximal side of the pulling member 104 (second pulling member 112), the deformation-held state is released. An operation portion 149 is mounted at the proximal end (proximal end of two wires) of the pulled state release wire 108. The pulled state release wire 108 is made of a material which can be cut Alternatively the operation portion 149 may be removed from the pulled state release wire 108. Therefore by cutting the pulled state release wire 108 or removing the operation portion 149 from the pulled state release wire 108, the end of the pulled state release wire 108 is formed or exposed. By pulling the pulled state release wire 108, it can be separated from the pulling member 104.

As the pulling wire and the unlocking wire, a wire or a plurality of twisted wires can be preferably used. Although not specifically limited, the diameter of the pulling wire and the unlocking wire is favorably in the range from 0.01 mm to 1.3 mm and more favorably in the range from 0.1 mm to 0.3 mm. As the material for forming the pulling wire and the unlocking wire, it is possible to use metals such as stainless steel, Ni—Ti alloy, Cu—Zn alloy, Ni—Al alloy, tungsten, tungsten alloy, titanium, titanium alloy, cobalt alloy, tantalum; comparatively rigid polymeric materials such as polyamide, polyimide, ultra-high-molecular-weight polyethylene, polypropylene, fluororesin; and a combination of these materials.

As shown in FIGS. 2, 3, 16, and 17, like the device 1 of the above-described embodiment, a contrast portion may be formed at the distal portion of the first part 201. A contrast portion may be formed at the distal portion of the second part and/or the proximal portion thereof A contrast portion may be formed at the distal portion of the third part 203 and/or the proximal portion thereof. In the examples shown in FIGS. 2, 3, 16, and 17, the contrast portions are formed at positions a little inward from the distal or proximal ends of each of the first, second, and third parts, but may be formed at the distal or proximal ends thereof.

The positions of these contrast portions can be checked by X-ray contrast and ultrasonic wave contrast It is preferable to compose the contrast portion of a ring-shaped wire or a coiled linear wire. As the material of the contrast portion, gold, platinum, tungsten, and alloys of these metals, a silver-palladium alloy can be preferably used. The contrast portion may be made of the same material as that used for the cylindrical members or a combination of a contrast substance and a material compatible therewith. As the contrast substance, it is possible to use X-ray unpermeable materials such as barium sulfate, bismuth oxide, and tungsten. A contrast portion (not shown) may be formed at the distal portion of the outer tube 140. It is possible to form the contrast portion at the distal portion of the outer tube 140 by a method similar to the method of forming the above-described contrast portions.

The method of using the apparatus having the device of the above-described embodiments is described below with reference to FIGS. 23 through 25.

As shown in FIGS. 12 through 15, the apparatus 110 is inserted into the femoral vein. Thereafter a guide wire (not shown) is inserted into the apparatus (between the outer tube 140 and the inner tube 141) 110 to insert the apparatus 110 into the lower large vein and then the right atrium of heart along the guide wire. Then the distal portion of the guide wire is passed through a foramen ovale of the interatrial septum. Thereafter the device 200 is pressed out of the distal end of the outer tube 140 of the apparatus 110 to dispose the first part 201 at the left atrium of heart with respect to the septum primum and dispose the second part 202 at the foramen ovale. Then with the distal position of the inner tube 141 held at its original position, the outer tube 140 is pulled toward its proximal side to expose the third part 203 inside the right atrium of heart After the entire device 200 is exposed in the heart, the pulling wire 148 is pulled. As a result, as shown in FIG. 25, the deformed state holding member 105 contacts the distal portion of the inner tube 141. By continuing to pull the pulling wire 148, the deformed state holding member 105 moves to the distal side of the pulling member (second pulling member 112). In a short time, the first part 201 bends. As a result the proximal portion of the first part 201 and the distal portion of the second part 202 become proximate to each other. Then the third part 203 bends. As a result, the distal portion of the third part 203 and the proximal portion of the second part 202 become proximate to each other. Consequently the body member of the device 200 deforms into a configuration similar to the letter "Z". The deformed state holding member 105 remains disposed on the pulling member (second pulling member 112), thereby keeping the device 200 deformed in the configuration similar to the letter "Z". In this manner, the first part 201 and the second part 202 hold the distal portion of the flap of the septum primum, and the second part 202 and the third part 203 hold an upper portion of the interatrial septum where the foramen ovale is present Thereby the flap is restrained from opening toward the left atrium of heart.

When an object is achieved in the deformed configuration of the device 200 similar to the letter "Z", the pulling wire 148 is cut at a position outward from the proximal end of the apparatus 110 and pulled out. Similarly, the pulled state release wire 108 is also cut at a position outward from the proximal end of the apparatus 110 and pulled out Thereafter the apparatus 110 (outer tube 140 and inner tube 141) is pulled out of the organism, together with the guide wire.

The device of the present invention for treating the patent foramen ovale has the first part having the predetermined length; the second part having the predetermined length; the third part having the predetermined length; and the pulling member whose proximal end penetrates into the second part from the side face of the distal portion of the second part, crosses the second cylindrical part obliquely and extends from the side face of the proximal portion of the second part and penetrates or is penetrable into the third part from the side face of the distal portion of the third part, with the distal end of the pulling member held by the proximal portion of the first part A part of the locking mechanism provided at the proximal portion of the pulling member and a part of the locking mechanism provided at the third part are locked to each other, when the pulling member is pulled to allow the first part and the second part to be proximate to each other and the second part and the third part to be proximate to each other.

What is claimed is:

1. A device for treating a patent foramen ovale comprising:
   a first part having a predetermined length;
   a second part having a predetermined length;
   a third part having a predetermined length;
   a first connection portion bendably connecting a proximal end of said first part and a distal end of said second part to each other;
   a second connection portion bendably connecting a position, located at a proximal end of said second part, which obliquely confronts said first connection portion and a distal end of said third part to each other, a pulling member penetrating into said second part from a side face of a distal portion of said second part, crossing said second part and extends from a side face of a proximal portion of said second part, and penetrating or being penetrable into said third part from a side face of a distal portion of said third part, with one end of said pulling member held by said first part, and a pair of a locking mechanism provided at other end of said pulling member and said third part being locked to each other, when said pulling member is pulled to allow said first part and said second part to proximate to each other and said second part and said third part to be proximate to each other;

wherein said one end of said pulling member held at a position of said first part in the vicinity of said first connection portion, said pulling member penetrates into said second part from a position of said side face of said distal portion of said second part in the vicinity of said first connection portion, extends from a position of said side face of said proximal portion of said second part in the vicinity of said second connection portion, and penetrates into said third part from a position of said side surface of said distal portion of said third part in the vicinity of said second connection portion.

2. A device according to claim 1, wherein said first part is a first cylindrical or columnar part; said second part is a second cylindrical or columnar part; and said third part is a third cylindrical or columnar part.

3. A device according to claim 1, wherein said locking mechanism comprises an anchoring portion provided at said other end portion of said pulling member; and a locking portion, provided at said third part, which permits a passage of said anchoring portion and locks said anchoring portion thereto after said anchoring portion passes therethrough.

4. A device according to claim 3, wherein said anchoring portion is provided plurally along said pulling member.

5. A device according to claim 3, wherein said locking portion is composed of a side hole permitting a passage of said anchoring portion and locking said anchoring portion thereto after said anchoring portion passes therethrough.

6. A device according to claim 3, wherein said locking portion is provided plurally along an axial direction of said third part.

7. An apparatus, for treating a patent foramen ovale, which is formed on a septum in an organism, comprising:
an outer tube;
a device, according to claim 1, accommodated inside a distal portion of said outer tube with said device kept almost straight;
an inner tube for pressing said device out of a distal end of said outer tube; and
a pulling wire for pulling said pulling member separably from said pulling wire.

8. An apparatus according to claim 7, wherein said pulling member of said device has an annular portion at a proximal end thereof; and said pulling wire is folded back after said pulling wire penetrates through said annular portion.

9. An apparatus according to claim 7, further comprising an unlocking mechanism for releasing locking performed by said locking mechanism of said device.

10. An apparatus according to claim 9, wherein said unlocking mechanism is composed of an unlocking wire, having a loop, which is disposed in said apparatus; and said pulling member or said pulling wire penetrates through said loop of said unlocking wire.

* * * * *